Figure 1:
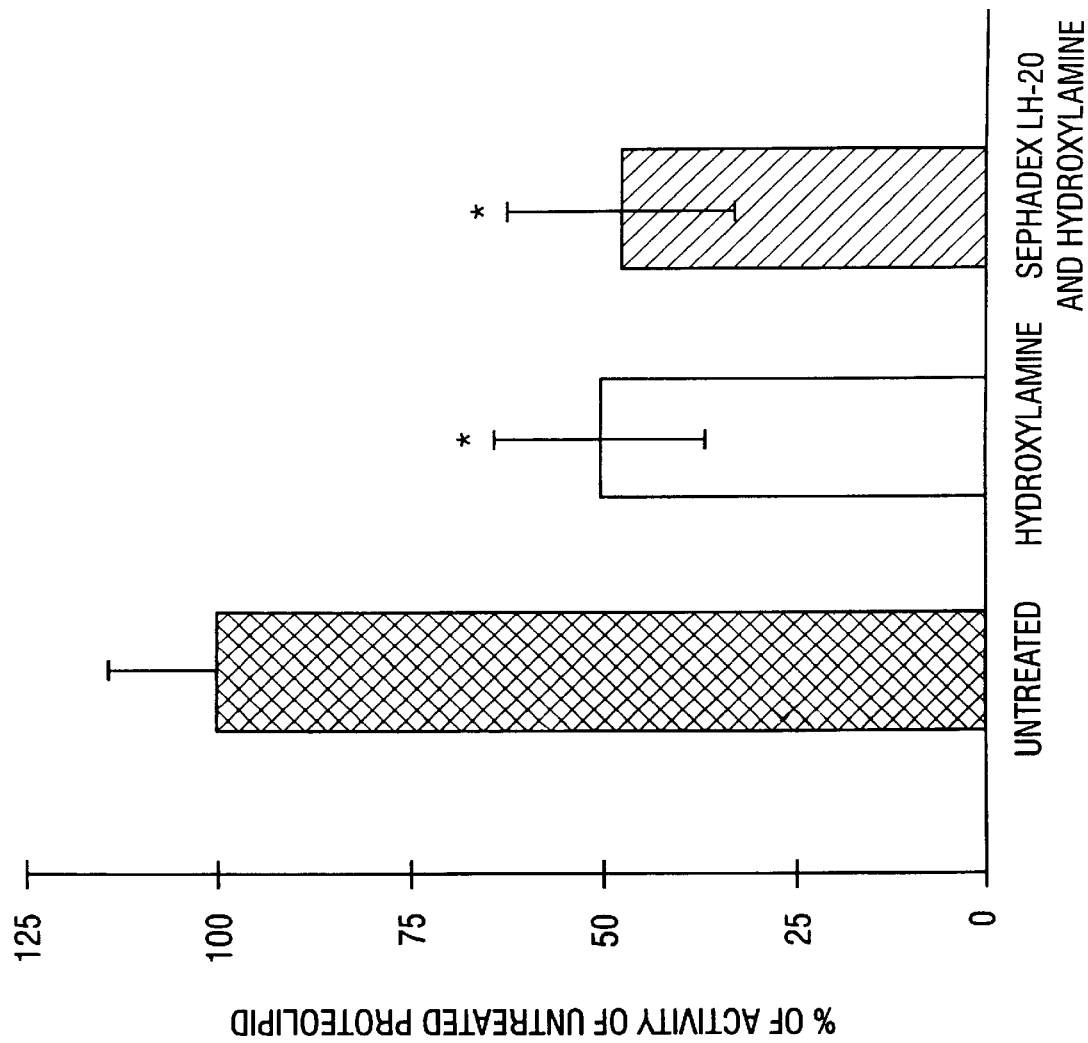

United States Patent [19]
Boyan et al.

[11] Patent Number: 5,989,907
[45] Date of Patent: Nov. 23, 1999

[54] METHODS AND COMPOSITIONS FOR CALCIUM BINDING PROTEOLIPID ENCODING NUCLEIC ACIDS

[75] Inventors: Barbara D. Boyan; Simon Van Dijk; David D. Dean, all of San Antonio, Tex.

[73] Assignee: Board of Regents, University of Texas System, Austin, Tex.

[21] Appl. No.: 08/780,836

[22] Filed: Jan. 10, 1997

Related U.S. Application Data

[60] Provisional application No. 60/009,798, Jan. 11, 1996, abandoned.

[51] Int. Cl.$^6$ .............................. C12N 15/85; C12N 1/21; C07H 21/02; C07H 21/04
[52] U.S. Cl. ................. 435/325; 425/252.3; 425/254.11; 425/320.1; 536/23.7; 536/24.32; 536/24.33
[58] Field of Search ........................... 435/6, 70.1, 320.1, 435/243, 252.3, 254.11, 325; 536/23.1, 23.2, 23.7, 24.3, 24.32, 24.33

[56] References Cited

PUBLICATIONS

Boyan, R., "Amino Terminal Sequence for *Corynebacterium matruchotii* Calcifiable Proteolipid," The FASEB Journal, 5(4):A814, 1991. (abstract).

Boyan et al., "Mechanisms of Bacterial Involvement in Dental Calculus Formation," Journal of Dental Research, 71 (special issue):233, 1992. (abstract).

Boyan–Salyers and Boskey, "Relationship Between Proteolipids and Calcium–Phosopholipid–Phosphate Complexes in *Bacterionema matruchotii* Calcification," Calcified Tissue International, 30(2):167–174, 1980.

Ennever et al., "Characterization of *Bacterionema matruchotii* Calcification Nucleator," Journal of Dental Research, 57(4):637–642, 1978.

Khare et al., "Immunoreactivity of Antibody to *Bacterionema matruchotti* Proteolipid," Journal of Dental Research, 67(special issue):233, 1998. (abstract).

Murakami, Y. "Analysis of the Nucleotide Sequences of Chromosome VI form *Saccharomyces cerevisiae*," Nature Genetics, 10(3):261–268, 1995.

Murakami, Y., EMBL Database Entry SCCHRVI Accession No. D50617, D44605, May 30, 1995.

Swain et al., "Resolution of Ion Translocating Proteolipid Subclasses Active in Bacterial Calcification," Journal of Dental Research, 68(6):1094–1097, 1989.

Internation Search Report dated Jun. 10, 1997, (UTFK:301P–).

Cao et al., "Characterization, Cloning and Expression of the 67–kDa Annexin from Chicken Growth Plate Cartilage Matrix Vesicles," Biochemical and Biophysical Research Communications, 197(2)556–561, 1993.

Genge et al., "Matrix Vesicle Annexins Exhibit Proteolipid–like Properties. Selective Partitioning into Lipophilic Solvents Under Acidic Conditions," The Journal of Biological Chemistry, 266(16):10678–10685, 1991.

Genge et al., "Establishment of the Primary Structure of the Major Lipid–Dependent $Ca^{2+}$ Binding Proteins of Chicken Growth Plate Cartilage Matrix Vesicles: Identity with Anchorin CII (Annexin V) and Annexin II," Journal of Bone and Mineral Research, 7(7):807–819, 1992.

Hemmings et al., "α– and β–Forms of the 65–kDa Subunit of Protein Phosphatase 2A Have a Similar 39 Amino Acid Repeating Structure," Biochemistry, 29(13):3166–3173, 1990.

Iakovidis et al., "Oral Micro–organisms and Calcific Aortic Stenosis," Abstracts from the 65th Scientific Sessions, Abstract No. 3380, Circulation 86:I–849, 1992.

Kessler et al., "Binding of Calcium to the Proteolipid Phosphorin," Mineral Electrolyte Metab., 14:135–141, 1988.

Van Dijk et al., "Immunological Detection of Bacterial Proteolipids Involved in Microbial Calcification," 75th General Session and Exhibition of the International Association for Dental Research; J. Dent. Res., vol. 76, Abstract No. 102, p. 26, 1997.

Van Dijk et al., "Sequencing of Bacterial Proteolipids Involved in Microbial Calcification," 74th General Session and Exhibition of the International Association for Dental Research; J. Dent Res., vol. 75, Abstract No. 614, p. 94, 1996.

Wu et al., "Characterization of the Nucleational Core Complex Responsible for Mineral Induction by Growth Plate Cartilage Matrix Vesicles," The Journal of Biological Chemistry, 268(33):25084–25094, 1993.

Murakami et al, Nature Genet. 10(3):261–268 (1995).

*Primary Examiner*—Patricia A. Duffy
*Attorney, Agent, or Firm*—Williams, Morgan & Amerson

[57] ABSTRACT

The present invention relates to the cloning and sequencing of DNA encoding membrane-associated proteolipids from *C. matruchotii* to vectors comprising the DNA and to host cells containing vectors including the novelty DNA.

17 Claims, 10 Drawing Sheets

1        5            10              15
Ala-Gly-Val-Pro-Gly-Val-Thr-Lys-Asn-Ser(P)-Ser-Gly-Ser(P)-Ala-Glu-Val-
                20            25              30      32
Lys-Lys-Leu-Lys-Val-Gly-Asp-Gly-Ser(P)-Ser-Lys-Ser-Glu-Ala-Asn-Phe

FIG. 5

```
  1                    5                  10                  15                 20
(Met) Asp Tyr Gly Gln Ile Ala Glu Gln Leu Gly Asn Phe Lys Lys Phe Ala Glu Ala Ile
                      25                 30                  35                 40
Gly Gly Ile Phe Thr Glu Leu Pro Lys Phe Leu Asn Asn Leu Asp Ser Phe Val Gly Gly
                      45                 50
Gly Arg Ser Ser Glu Gly Leu Gly Glu Thr
```

FIG. 6A

```
  1                    5                  10                  15                 20
(Met) Asp Tyr Gly Gln Ile Ala Glu Gln Leu Gly Asn Phe Lys Lys Phe Ala Glu Ala Ile
                      25                 30                  35                 40
Gly Gly Ile Phe Thr Glu Leu Pro Lys Phe Leu Asn Asn Leu Asp Ser Phe Val Gly Gly
                      45    47
Gly Arg Ser Ser Glu Gly Leu
```

FIG. 6B

```
nt    1  ─── primer pp6-N5 ───
      CG GAATTC ATG GAT TAC GGN CAG ATC GCT GAG CAG CTT GGC AAC TTC AAG AAG
            EcoRI  Met Asp Tyr Gly Gln Ile Ala Glu Gln Leu Gly Asn Phe Lys Lys
                                         30
```

```
                                                                    90
TTC GCT GAG GCC ATT GGT GGT ATC TTC ACC GAG CTA CCC AAG TTC CTC AAC
Phe Ala Glu Ala Ile Gly Gly Ile Phe Thr Glu Leu Pro Lys Phe Leu Asn
                     60
```

```
                                           120
AAC CTT GAC AGC TTT GTT GGT GGT GGC CGC GGT AGC TCC GAA CTN GGC
Asn Leu Asp Ser Phe Val Gly Gly Gly Arg Gly Ser Ser Glu Leu Gly
```

```
      150
 ─── primer pp6-N5 ───
GAA ACC GGATCC GC
Glu Thr  BamHI
```

FIG. 8

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
           (A) LENGTH: 50 amino acids
           (B) TYPE: amino acid
           (C) STRANDEDNESS: single
           (D) TOPOLOGY: linear (xi) SEQUENCE DESCRIPTION: SEQ ID NO:1:

Met Asp Tyr Gly Gln Ile Ala Glu Gln Leu Gly Asn Phe Lys Lys Phe
1               5                   10                  15

Ala Glu Ala Ile Gly Gly Ile Phe Thr Glu Leu Pro Lys Phe Leu Asn
            20                  25                  30

Asn Leu Asp Ser Phe Val Gly Gly Gly Arg Gly Ser Ser Glu Leu Gly
        35                  40                  45

Glu Thr
    50

(2) INFORMATION FOR SEQ ID NO:2:

(i) SEQUENCE CHARACTERISTICS:
           (A) LENGTH: 32 amino acids
           (B) TYPE: amino acid
           (C) STRANDEDNESS: single
           (D) TOPOLOGY: linear (xi) SEQUENCE DESCRIPTION: SEQ ID NO:2:

Ala Gly Val Pro Gly Val Thr Lys Asn Ser Ser Gly Ser Ala Glu Val
1               5                   10                  15

Lys Lys Leu Lys Val Gly Asp Gly Ser Ser Lys Ser Glu Ala Asn Phe
            20                  25                  30

(2) INFORMATION FOR SEQ ID NO:3:

(i) SEQUENCE CHARACTERISTICS:
           (A) LENGTH: 150 base pairs
           (B) TYPE: nucleic acid
           (C) STRANDEDNESS: single
           (D) TOPOLOGY: linear (ix) FEATURE:
           (A) NAME/KEY: modified_base
           (B) LOCATION: one-of(12, 141)
           (D) OTHER INFORMATION: /note= "N = A, C, G or T"

(xi) SEQUENCE DESCRIPTION: SEQ ID NO:3:

ATGGATTACG GNCAGATCGC TGAGCAGCTT GGCAACTTCA AGAAGTTCGC TGAGGCCATT      60

GGTGGTATCT TCACCGAGCT ACCCAAGTTC CTCAACAACC TTGACAGCTT TGTTGGTGGT    120

GGCCGCGGTA GCTCCGAACT NGGCGAAACC                                     150

(2) INFORMATION FOR SEQ ID NO:4:

(i) SEQUENCE CHARACTERISTICS:
           (A) LENGTH: 6 amino acids
           (B) TYPE: amino acid
           (C) STRANDEDNESS: single
           (D) TOPOLOGY: linear (xi) SEQUENCE DESCRIPTION: SEQ ID NO:4:

```
Ala Gly Val Pro Gly Val
1               5
```

(2) INFORMATION FOR SEQ ID NO:5:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO:5:

```
Met Asp Tyr Gly Gln Ile Ala Glu Gln Leu Gly Asn Phe Lys Lys
1               5                  10                  15
```

(2) INFORMATION FOR SEQ ID NO:6:

(i) SEQUENCE CHARACTERISTICS:
        (A) LENGTH: 166 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 9..158

(ix) FEATURE:
        (A) NAME/KEY: modified_base
        (B) LOCATION: one-of(20, 149)
        (D) OTHER INFORMATION: /note= "N = A, C, G or T"

(xi) SEQUENCE DESCRIPTION: SEQ ID NO:6:

```
CGGAATTC ATG GAT TAC GGN CAG ATC GCT GAG CAG CTT GGC AAC TTC AAG      50
         Met Asp Tyr Xaa Gln Ile Ala Glu Gln Leu Gly Asn Phe Lys
          1               5                  10

AAG TTC GCT GAG GCC ATT GGT GGT ATC TTC ACC GAG CTA CCC AAG TTC      98
Lys Phe Ala Glu Ala Ile Gly Gly Ile Phe Thr Glu Leu Pro Lys Phe
 15              20                  25                  30

CTC AAC AAC CTT GAC AGC TTT GTT GGT GGT GGC CGC GGT AGC TCC GAA     146
Leu Asn Asn Leu Asp Ser Phe Val Gly Gly Gly Arg Gly Ser Ser Glu
             35                  40                  45

CTN GGC GAA ACC GGATCCGC                                            166
Xaa Gly Glu Thr
         50
```

(2) INFORMATION FOR SEQ ID NO:7:

(i) SEQUENCE CHARACTERISTICS:
        (A) LENGTH: 50 amino acids
        (B) TYPE: amino acid
        (D) TOPOLOGY: linear (ii) MOLECULE TYPE: protein (xi) SEQUENCE DESCRIPTION: SEQ ID NO:7:

```
Met Asp Tyr Xaa Gln Ile Ala Glu Gln Leu Gly Asn Phe Lys Lys Phe
1               5                  10                  15

Ala Glu Ala Ile Gly Gly Ile Phe Thr Glu Leu Pro Lys Phe Leu Asn
             20                  25                  30

Asn Leu Asp Ser Phe Val Gly Gly Gly Arg Gly Ser Ser Glu Xaa Gly
         35                  40                  45

Glu Thr
     50
```

(2) INFORMATION FOR SEQ ID NO:8:

(i) SEQUENCE CHARACTERISTICS:
        (A) LENGTH: 47 amino acids
        (B) TYPE: amino acid
        (C) STRANDEDNESS: single
        (D) TOPOLOGY: linear (xi) SEQUENCE DESCRIPTION: SEQ ID NO:8:

Met Asp Tyr Gly Gln Ile Ala Glu Gln Leu Gly Asn Phe Lys Lys Phe
1               5                   10                  15

Ala Glu Ala Ile Gly Gly Ile Phe Thr Glu Leu Pro Lys Phe Leu Asn
            20                  25                  30

Asn Leu Asp Ser Phe Val Gly Gly Arg Gly Ser Ser Glu Leu
        35                  40                  45

(2) INFORMATION FOR SEQ ID NO:9:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 23
        (D) OTHER INFORMATION: /note= "R = A or G"

(ix) FEATURE:
        (A) NAME/KEY: modified_base
        (B) LOCATION: one-of(14, 17, 20)
        (D) OTHER INFORMATION: /note= "Y = C or T"

(xi) SEQUENCE DESCRIPTION: SEQ ID NO:9:

CGGAATTCAT GGAYTAYGGY CARATC                                  26

(2) INFORMATION FOR SEQ ID NO:10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: one-of(9, 15, 24)
        (D) OTHER INFORMATION: /note= "R = A or G"

(ix) FEATURE:
        (A) NAME/KEY: modified_base
        (B) LOCATION: 18
        (D) OTHER INFORMATION: /note= "W = A or T"

(ix) FEATURE:
        (A) NAME/KEY: modified_base
        (B) LOCATION: one-of(12, 21)
        (D) OTHER INFORMATION: /note= "Y = C or T"

(xi) SEQUENCE DESCRIPTION: SEQ ID NO:10:

GCGGATCCRG TYTCRCCWAG YTCRGA                                  26

(2) INFORMATION FOR SEQ ID NO:11:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:11:

CGGAATTCGC AGGCGTTCCA GGCGTTACCA AGAA                         34

(2) INFORMATION FOR SEQ ID NO:12:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:12:

GCGGATCCCT CGGACTTGGA GGAGCCGTCG CCAAC        35

METHODS AND COMPOSITIONS FOR CALCIUM BINDING PROTEOLIPID ENCODING NUCLEIC ACIDS

This claims priority to provisional patent application Ser. No. 60/009,798 filed Jan. 11, 1996 now abandoned.

The United States Government has rights in the present invention pursuant to support from National Institute of Dental Research grants DE-07263, DE-05932 and National Science Foundation grant EEC-92/09612.

1.0 BACKGROUND OF THE INVENTION

1.1 Field of the Invention

The present invention relates to the fields of protein chemistry and immunology; in particular to the isolation and characterization of new calcium binding proteolipids, the encoding DNA and to methods of using the novel proteins for detection of calcifying bacteria in various pathological conditions such as dental calculus and heart valve calcification.

1.2 Description of Related Art

Numerous studies have implicated oral bacteria in the etiology of transient bacteremia and endocarditis (Everett and Hirschmann, 1977). In particular, some studies have indicated that *C. matruchotii* may play a role in the occurrence of bacterial endocarditis and in the calcification of bicuspid heart valves (Cohen et al., 1992; Iakovidis et al., 1992).

*Corynebacterium matruchotii* is a microbial inhabitant of the oral cavity associated with dental calculus formation. As early as 1925, *C. matruchotii* (previously known as *Leptothrix buccalis* and *Bacterionema matruchotii*) was shown to be present in calcified deposits scraped from teeth (Bulleid, 1925). Subsequently it was demonstrated that these calcium phosphate containing deposits were due to bacteria in the dental calculus and that their production was regulated by various environmental factors (Ennever, 1960; Wasserman et al., 1958; Zander et al., 1960). At the light and electron microscopic level, mineralization in these bacteria has been found to occur either intracellularly, as in *Actinomyces israeli, Escherichia coli, Streptococcus sanguis, Streptococcus mutans, Streptococcus salivarius*, and some strains of *C. matruchotii*, or extracellularly, as in *Veillonella* and the diphtheroids (Ennever etal., 1974; Lie and Selvig, 1974; Rizzo et al., 1962; Streckfuss et al., 1974; Wasserman et al., 1958). The mineralized deposits produce electron diffraction patterns similar to that found in mammalian bone (Boyan-Salyers et al., 1978b; Ennever et al., 1971; Gonzales and Sognnaes, 1960). Also similarly to bone formation (Anderson, 1969), initial deposition of hydroxyapatite in calcifying bacteria has been associated with membranes (Ennever et al., 1968; Ennever et al., 1971; Vogel and Smith, 1976) or membrane components (Boyan and Boskey, 1984; Boyan-Salyers et al., 1978b; Boyan-Salyers and Boskey, 1980; Ennever et al., 1972; Ennever et al., 1976; Ennever et al., 1979).

Calcification of *C. matruchotii* has been examined using a number of in vitro models (Boyan-Salyers et al., 1978b; Ennever et al., 1971; Lie and Selvig, 1974; Vogel and Smith, 1976). Because mineralization will not occur without an adequate calcium supply, *C. matruchotii* can be studied under either calcification-permissive or calcification-nonpermissive conditions (Boyan et al., 1984; Boyan-Salyers and Boskey, 1980; Ennever et al., 1971), making it an excellent model for studying mineralization in general, and microbial calcification in particular. The initial steps in apatite formation involve $Ca^{2+}$-binding to acidic phospholipids, particularly phosphoinositides and phosphatidylserine (Boyan-Salyers and Boskey, 1980; Vogel et al., 1978), followed by the addition of inorganic phosphate and $Ca^{2+}$ to form apatite $[Ca_{10}(PO_4)_6]$ clusters that are converted by hydration to hydroxyapatite (Vogel and Boyan-Salyers, 1976). It is believed that the acidic phospholipids in the membrane associate with specific proteolipids to form a complex which directs the initial phases of the process (Boyan et al., 1992; Boyan and Boskey, 1984; Boyan-Salyers et al., 1978a; Ennever et al., 1976; Raggio et al., 1986; Vogel and Boyan-Salyers, 1976).

Previous studies have demonstrated that calcifiable proteolipids isolated from *C. matruchotii* are involved in ion translocation across lipid bilayers. Using reconstituted bacteriorhodopsin-proteoliposomes, translocation of ions across the membrane was greatly enhanced in the presence of proteolipids extracted from *C. matruchotii* (Boyan et al., 1992; Swain et al., 1989; Swain and Boyan, 1988). Ion-transport across the liposomal membrane was inhibited by dicyclohexylcarbodiimide (DCCD, an inhibitor of proton channels). It has been suggested that proteolipids form an ionophore that could play a role in the intracellular accumulation of calcium and phosphate ions or export of protons, followed by initial mineralization on the inner leaflet of the membrane (Boyan et al., 1989a; 1989b; 1992; Swain and Boyan, 1988; 1989).

A number of studies have shown that calcifiable bacteria contain constituents which can support calcification under appropriate conditions. Membranes isolated from *C. matruchotii* provide nucleating foci for apatite formation in vitro (Ennever et al., 1976; Vogel and Smith, 1976). More recent data indicate that specific calcifiable proteolipids permit the ordered structuring of phospholipids in the cell membrane so that calcium-acidic phospholipid-phosphate complexes (CPLX) can form (Boyan et al., 1992; Boyan and Boskey, 1984; Boyan-Salyers and Boskey, 1980; Raggio et al., 1986).

Previous work has reported a 8–10 kDa proteolipid involved in *C. matruchotii* calcification (Boyan, 1985). In an earlier paper, phospholipids were reported to be associated with the protein moiety through hydrophobic interactions (Ennever et al., 1973); with partial removal of this phospholipid resulting in loss of calcifiability (Ennever et al., 1978a; 1978b). Later studies demonstrated the presence of additional proteolipids in the bacteria (Swain et al., 1989), which enhanced ion transport across liposomal membranes.

It has been suggested that proteolipids might function in two capacities during calcification: as sites for CPLX formation and in transport of $Ca^{2+}$ and $P_i$ to the calcification site or in the transport of protons away from the site (Boyan et al., 1989a; Swain and Boyan, 1989).

Proteolipids have been reported to play a role in both calcium binding in growth plate cartilage matrix vesicles (Cao et al., 1993; Genge et al., 1991; 1992) and phosphate binding and transport over kidney brush border membranes (Debiec and Lorenc, 1988; Kessler et al., 1982; 1988). In matrix vesicles a nucleational core complex, reminiscent of CPLX, has been reported, consisting of a membrane associated complex of $Ca^{2+}$, $P_i$, phosphatidylserine and annexins, proteins exhibiting proteolipid-like characteristics, and capable of initiating nucleation (Genge et al., 1991; Wu et al., 1993). On the other hand, phosphate transport across kidney brush border membranes has been associated with phosphorin, a 3 kDa membrane proteolipid (Kessler et al., 1982), as well as with a proteolipid-like Na$^+$,P$_i$-binding protein with a molecular mass of 155 kDa (Debiec and Lorenc, 1988).

2.0 SUMMARY OF THE INVENTION

The present invention relates to the isolation and characterization of a novel proteolipid "bacteriocalcifin",from *C. matruchotii* that is involved in the formation of dental calculus ("plaque") and heart valve calcification. The new proteolipid represents a new class of calcium binding species designated "bacteriocalcifins".

The present invention provides biologically active proteolipids comprising the amino acid sequences of bacteriocalcifin-1(SEQ ID NO:1) (5.5 kilodalton proteolipid, designated "bacteriocalcifin-1") and bacteriocalcifin-2 (SEQ ID NO:2) (7.5 kilodalton proteolipid), as well as the nucleotide sequence of the bcf-1 gene for the 5.5 kilodalton proteolipid of (SEQ ID NO:3) and (SEQ ID NO:6) that includes the sequence of (SEQ ID NO:3) encoding a 5.5 kDa bacteriocalcifin. Among the biological properties of the bacteriocalcifins in the present invention is the capability to induce the formation of hydroxyapatite in vivo and the binding of calcium in an in vitro assay system.

An important aspect of the invention concerns the isolation, characterization, amino acid sequencing, cloning and nucleotide sequencing of the proteolipid from *C. matruchotii*, as well as the assay to determine in vitro calcification activity. The invention also contains the generation of polyclonal and monoclonal antibodies against the proteolipid fraction from *C. matruchotii* and their use in the detection of the proteolipid in immunoblots, ELISA-assays and in the use of blocking calcium binding activity in an in vitro calcification assay.

The present invention includes the isolation and characterization of a novel protein with an apparent MW of 5.5 kilodaltons after SDS-polyacrylamide gel electrophoresis from the oral bacterium *Corynebacterium matruchotii* which is involved in the formation of dental calculus ("plaque") and heart valve calcification. Characteristics of the calcium binding protein complex include:

(a) a unique amino acid sequence;
(b) lipid molecules covalently attached to a protein core;
(c) a novel 5.5 kilodalton protein that is a bacterial homolog of a mammalian phosphoprotein phosphatase; and
(d) is involved in calcification of *C. matruchotii*.

Additionally, the invention describes the generation of polyclonal and monoclonal antibodies against bacterial phosphoprotein phosphatase. The antibodies may be used to detect the presence of *C. matruchotii* in the oral cavity and in pathological septic calcified deposits. The antibodies are also useful in detecting the presence of phosphoprotein phosphatase and related proteins in cultures of *C. matruchotii* and other calcifiable bacteria. The antibodies may be used to block the activity of the disclosed calcium binding proteins and are expected to find use in blocking the formation of dental calculus and heart valve calcification.

2.1 Novel Calcium Binding Polypeptides

In an important aspect therefore, the present invention relates to the discovery of a novel proteolipid calcium-binding protein isolated from *Cornyebacterium matruchotii*. The intact proteolipid comprises three apoproteins covalently attached to a lipid and has an apparent molecular weight of approximately 10 kDa. The proteolipid polypeptide components do not show substantial homology with calcifying strains of Streptococcus, e.g., *S. sanguis*, type II.

One of the three apoproteins has an apparent molecular weight of 5.5 kDa by SDS PAGE and appears to be a bacterial homolog of mammalian pliosphoprotein phosphatase. The amino acid sequence of the apoprotein has been determined in accordance with SEQ ID NO:1 and an N-terminal sequence in accordance with SEQ ID NO:5.

A second apoprotein has an apparent molcular weight of 7.5 kDa by SDS-PAGE. A partial peptide sequence (SEQ ID NO:2) represents the N-terminal sequence.

The third apoprotein has an apparent molecular weight of 5.0 kDa by SDS-PAGE. Its amino acid sequence is in accordance with SEQ ID NO:8. The partial amino acid sequence representing the N-terminal sequence is represented by SEQ ID NO:5.

2.2 Pharmaceutical Compositions

Another aspect of the present invention includes novel compositions comprising isolated and purified apoproteins, proteolipids or nucleic acids which encode the disclosed proteolipid calcium binding protein. Regarding nucleic acids, it will, of course, be understood that one or more than one calcium-binding proteolipid gene may be used in the methods and compositions of the invention. The nucleic acid delivery methods may thus entail the administration of one, two, three, or more, homologous genes. The maximum number of genes that may be applied is limited only by practical considerations, such as the effort involved in simultaneously preparing a large number of gene constructs or even the possibility of eliciting an adverse cytotoxic effect.

With regard to the calcium-binding protein and proteolipid compositions, it is contemplated that such compositions will contain a biologically effective amount of the novel peptide, peptides or lipid associated forms of such peptides. As used herein a "biologically effective amount" of a peptide or composition refers to an amount effective to stimulate or promote calcium binding. As disclosed herein, different peptide amounts may be effective, as shown in vitro, such as may be effective in vivo between about 6 to about 11 mg/kg.

Clinical doses will of course be determined by the nutritional status, age, weight and health of the patient. The quantity and volume of the peptide composition administered will depend on the subject and the route of administration. The precise amounts of active peptide required will depend on the judgment of the practitioner and may be peculiar to each individual. However, in light of the data presented herein, the determination of a suitable dosage range for use in humans will be straightforward.

The compositions for use in stimulating antibodies for blocking calcium binding in accordance with the present invention will be compositions that contain the full length peptide or partial sequences including effective epitopes. The term "a peptide" or "a polypeptide" in this sense means at least one peptide or polypeptide which includes a sequence of any of the aforementioned structures or variants thereof. The terms peptide, polypeptide, or protein may be used interchangeably.

In addition to including an amino acid sequence in accordance with SEQ ID NO:1, SEQ ID NO:2, SEQ ID NO:4, or SEQ ID NO:8, the peptides may include various other shorter or longer fragments or other short peptidyl sequences of various amino acids. In certain embodiments, the peptides may include shorter sequences, for example the N-terminal regions, SEQ ID NO:5 or SEQ ID:6, of the apoprotein or additional sequences such as short targeting sequences, tags, labelled residues, amino acids contemplated to increase the half life or stability of the peptide or any additional residue for a designated purpose, so long as the peptide still functions as a calcium binding agent and as such will stimulate antibodies to block this activity. Such functionality may be readily determined by assays such as those described herein.

Any of the commonly occurring amino acids may be incorporated into the peptides, including alanine, arginine, aspartic acid, asparagine, cysteine, glutamic acid, glutamine, glycine, histidine, isoleucine, leucine, lysine, methionine, phenylalanine, proline, serine, threonine, tryptophan, tyrosine and valine. Likewise, any of the so-called rare or modified amino acids may also be incorporated into a peptide of the invention, including: 2-Aminoadipic acid, 3-Aminoadipic acid, beta-Alanine (beta-Aminopropionic acid), 2-Aminobutyric acid, 4-Aminobutyric acid (piperidinic acid), 6-Aminocaproic acid, 2-Aminoheptanoic acid, 2-Aminoisobutyric acid, 3-Aminoisobutyric acid, 2-Aminopimelic acid, 2,4-Diaminobutyric acid, Desmosine, 2,2'-Diaminopimelic acid, 2,3-Diaminopropionic acid, N-Ethylglycine, N-Ethylasparagine, Hydroxylysine, allo-Hydroxylysine, 3-Hydroxyproline, 4-Hydroxyproline, Isoeesmosine, allo-Isoleucine, N-Methylglycine sarcosine), N-Methylisoleucine, N-Methylvaline, Norvaline, Norleucine and Ornithine.

The inhibitory compositions of the invention may include a peptide modified to render it biologically protected. Biologically protected peptides have certain advantages over unprotected peptides when administered to human subjects and, as disclosed in U.S. Pat. No. 5,028,592, incorporated herein by reference, protected peptides often exhibit increased pharmacological activity.

Compositions for use in the present invention may also comprise peptides which include all L-amino acids, all D-amino acids or a mixture thereof. The use of D-amino acids may confer additional resistance to proteases naturally found within the human body and are less immunogenic and can therefore be expected to have longer biological half lives.

Likewise, compositions that make use of calcium-binding proteolipid encoding genes are also contemplated. The particular combination of genes may be two or more variants of such genes; or it may be such that a calcium binding proteolipid gene is combined with another gene and/or another protein such as a alkaline, neutral or acid phosphatase, cofactor or other biomolecule; a hormone or growth factor gene may even be combined with a gene encoding a cell surface receptor capable of interacting with the polypeptide product of the first gene.

In using multiple genes, they may be combined on a single genetic construct under control of one or more promoters, or they may be prepared as separate constructs of the same or different types. Thus, an almost endless combination of different genes and ogenetic constructs may be employed. Certain gene combinations may be designed to, or their use may otherwise result in, achieving synergistic effects on cell growth and/or stimulation of an immune response. Any and all such combinations are intended to fall within the scope of the present invention. Indeed, many synergistic effects have been described in the scientific literature, so that one of ordinary skill in the art would readily be able to identify likely synergistic gene combinations, or even gene-protein combinations.

It will also be understood that, if desired, the nucleic acid segment or gene encoding a calcium binding proteolipid could be administered in combination with further agents, such as, e.g., proteins or polypeptides or various pharmaceutically active agents. So long as the composition comprises a calcium-binciing proteolipid gene, there is virtually no limit to other components which may also be included, given that the additional agents do not cause a significant adverse effect upon contact with the target cells or host tissues. The nucleic acids may thus be delivered along with various other agents as required in the particular instance.

Pharmaceutical compositions prepared in accordance with the present invention find use in several applications, including blocking of the formation of dental calculus and prevention of heart valve calcification. Such methods generally involve administering to a mammal a pharmaceutical composition comprising an immunologically effective amount of a calcium-binding proteolipid or apoprotein composition. This composition may include an immunologically-effective amount of either the apo- or lipoproteins herein described or their corresponding encoding nucleic acid composition. Such compositions would typically stimulate an immune response in a mammal.

Therapeutic kits comprising the aforementioned proteolipids, apoprotein components or corresponding-encoding nucleic acid segments comprise another aspect of the present invention. Such kits will generally contain, in suitable container means, a pharmaceutically acceptable formulation of a calcium-binding proteolipid, apoprotein or the encoding nucleic acid composition. The kit may have a single container means that contains the polypeptide composition or it may have distinct container means for the compositions and other reagents which may be included within such kits.

The components of the kit may be provided as liquid solution(s), or as dried powder(s). When the components are provided in a liquid solution, the liquid solution is an aqueous solution, with a sterile aqueous solution being particularly preferred. When reagents or components are provided as a dry powder, the powder can be reconstituted by the addition of a suitable solvent. It is envisioned that the solvent may also be provided in another container means.

In related embodiments, the present invention contemplates the preparation of diagnostic kits that may be employed to detect the presence of calcium-binding proteins or peptides and/or antibodies in a sample. Generally speaking, kits in accordance with the present invention will include a suitable calcium-binding protein or peptide or antibody directed against such a protein or peptide, together with an immunodetection reagent and a means for containing the antibody or antigen and reagent. The components of the diagnostic kits may be packaged either in aqueous media or in lyophilized form.

The immunodetection reagent will typically comprise a label associated with the antibody or antigen, or associated with a secondary binding ligand. Exemplary ligands might include a secondary antibody directed against the first antibody or antigen or a biotin or avidin (or streptavidin) ligand having an associated label. Of course, as noted above, a number of exemplary labels are known in the art and all such labels may be employed in connection with the present invention. The kits may contain antibody-label conjugates either in fully conjugated form, in the form of intermediates, or as separate moieties to be conjugated by the user of the kit.

The container means will generally include at least one vial, test tube, flask, bottle, syringe or other container means, into which the antigen or antibody may be placed, and preferably suitably aliquoted. Where a second binding ligand is provided, the kit will also generally contain a second vial or other container into which this ligand or antibody may be placed. The kits of the present invention will also typically include a means for containing the antibody, antigen, and reagent containers in close confinement for commercial sale. Such containers may include injection or blow-molded plastic containers into which the desired vials are retained.

2.3 Antibodies

In another aspect, the present invention includes an antibody that is immunoreactive with a polypeptide of the invention. An antibody can be a polyclonal or a monoclonal antibody. In a preferred embodiment, an antibody is a monoclonal antibody. Means for preparing and characterizing antibodies are well known in the art (See, e.g., Howell and Lane, 1988).

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of antisera is a rabbit, a mouse, a rat, a hamster or a guinea pig. Because of the relatively large blood volume of rabbits, a rabbit is a preferred choice for production of polyclonal antibodies.

Antibodies, both polyclonal and monoclonal, specific for the proteolipids or apoproteins associated with the proteolipids may be prepared using conventional immunization techniques, as will be generally known to those of skill in the art. A composition containing antigenic epitopes of the proteins can be used to immunize one or more experimental animals, such as a rabbit or mouse, which will then proceed to produce specific antibodies against the protein. Polyclonal antisera may be obtained, after allowing time for antibody generation, simply by bleeding the animal and preparing serum samples from the whole blood.

To obtain monoclonal antibodies, one would also initially immunize an experimental animal, often preferably a mouse, with a calcium-binding proteolipid or apoprotein of such a proteolipid composition. One would then, after a period of time sufficient to allow antibody generation, obtain a population of spleen or lymph cells from the animal. The spleen or lymph cells can then be fused with cell lines, such as human or mouse myeloma strains, to produce antibody-secreting hybridomas. These hybridomas may be isolated to obtain individual clones which can then be screened for production of antibody to the desired peptide.

Following immunization, spleen cells are removed and fused, using a standard fusion protocol with plasmacytoma cells to produce hybridomas secreting monoclonal antibodies against the calcium-binding proteolipid. Hybridomas which produce monoclonal antibodies to the selected antigens are identified using standard techniques, such as ELISA and Western blot methods. Hybridoma clones can then be cultured in liquid media and the culture supernatants purified to provide the calcium-binding proteolipid-specific monoclonal antibodies.

It is proposed that the monoclonal antibodies of the present invention will find useful application in standard immunochemical procedures, such as ELISA and Western blot methods, as well as other procedures which may utilize antibody specific to calcium-binding proteolipid epitopes.

Additionally, it is proposed that monoclonal antibodies specific to the particular chemokine may be utilized in other useful applications. For example, their use in immunoabsorbent protocols may be useful in purifying native or recombinant calcium-binding proteolipids from other bacterial species or variants thereof.

In general, both poly- and monoclonal antibodies against the proteolipids herein disclosed may be used in a variety of embodiments. For example, they may be employed in antibody cloning protocols to obtain cDNAs or genes encoding the proteolipid or related proteins. They may also be used in inhibition studies to analyze the effects of the proteolipid in cells or animals. Anti-calcium-binding proteolipid antibodies will also be useful in immunolocalization studies to analyze the distribution of calcium binding proteolipids during various cellular events, for example, to determine the cellular or tissue-specific distribution of such peptides under different physiological conditions. A particularly useful application of antibodies generated from the proteolipids is in purifying native or recombinant calcium-binding proteolipids, for example, using an antibody affinity column. The operation of all such immunological techniques will be known to those of skill in the art in light of the present disclosure.

2.7 Recombinant Polypeptides

Recombinant versions of a protein or polypeptide are deemed as part of the present invention. Thus one may, using techniques familiar to those skilled in the art, express a recombinant version of the polypeptide in a recombinant cell to obtain the polypeptide from such cells. The techniques are based on cloning of a DNA molecule encoding the polypeptide from a DNA library, that is, on obtaining a specific DNA molecule distinct from other DNAs. One may, for example, clone a cDNA molecule, or clone genomic DNA. Techniques such as these would also be appropriate for the production of the bacteriocalcifin polypeptides in accordance with the present invention.

2.8 Genes

As known to those of skill in the art, the original source of a recombinant gene or DNA segment to be used in a therapeutic regimen need not be of the same species as the animal to be treated. In this regard, it is contemplated that any recombinant calcium-binding proteolipid gene may be employed in the methods disclosed herein such as the identification of cells containing DNA encoding calcium-binding proteolipid or variants of the protein.

Particularly preferred genes are those isolated from bacteria, particularly *C. matruchotii* as well as closely related species, including other oral bacteria, such as *Actinomyces israeli, Streptococcus sanguis, S. mitis, S. salivarius,* Veillonella, the diptheroids, and certain strains of *Escherichia coli*. It is contemplated that homologous genes encoding proteolipids of similar calcium binding activity will be found in such other related species as *C. glutamicum. Brevibacterium flavum, Brevibacterium lactofermentum* and *Corynebacterium pseudotuberculosis*. However, since the sequence homology for genes encoding the protein may be conserved across species lines, equine, murine, and bovine species may also be contemplated as sources, in that such genes and DNA segments are readily available; however, with the bacterial forms of the gene being most preferred for use in treatment regimens. Recombinant proteins and polypeptides encoded by isolated DNA segments and genes are often referred to with the prefix "r" for recombinant and "rh" for recombinant human. As such, DNA segments encoding rcalcium-binding proteolipids, or rcalcium-binding proteolipid-related genes, etc. are contemplated to be particularly useful in connection with this invention. Any recombinant proteolipid gene would likewise be very useful with the methods of the invention.

The definition of a "calcium-binding proteolipid gene", as used herein, is a gene that hybridizes, under relatively stringent hybridization conditions (see, e.g., Maniatis et al., 1982), to DNA sequences presently known to include calcium-binding proteolipid gene sequences.

To prepare a calcium-binding proteolipid gene segment or cDNA one may follow the teachings disclosed herein and also the teachings of any of patents or scientific documents specifically referenced herein. One may obtain a rcalcium-binding proteolipid-encoding DNA segments using molecular biological techniques, such as polymerase chain reaction (PCR) or screening of a cDNA or genomic library, using primers or probes with sequences based on the above nucleotide sequence. Such fragments may be readily prepared by, for example, directly synthesizing the fragment by chemical means, by application of nucleic acid reproduction technology, such as the PCR technology of U.S. Pat. Nos. 4,683,195 and 4,683,202 (herein incorporated by reference). The practice of these techniques is a routine matter for those of skill in the art, as taught in various scientific texts (see e.g., Sambrook et al., 1989), incorporated herein by reference. Certain documents further particularly describe suitable mammalian expression vectors, e.g., U.S. Pat. No. 5,168,050, incorporated herein by reference. The genes and DNA segments that are particularly preferred for use in certain aspects of the present methods are those encoding bacterial calcium-binding proteolipids and related polypeptides.

It is also contemplated that one may clone further genes or cDNAs that encode a calcium-binding peptide, protein or polypeptide. The techniques for cloning DNA molecules, i.e., obtaining a specific coding sequence from a DNA library that is distinct from other portions of DNA, are well known in the art. This can be achieved by, for example, screening an appropriate DNA library which relates to the cloning of a calcium-binding gene such as the C. matruchotii proteolipids disclosed herein. The screening procedure may be based on the hybridization of oligonucleotide probes, designed from a consideration of portions of the amino acid sequence of known DNA sequences encoding related cytokine proteins. The operation of such screening protocols are well known to those of skill in the art and are described in detail in the scientific literature, for example, see Sambrook et al., 1989.

Techniques for introducing changes in nucleotide sequences that are designed to alter the functional properties of the encoded proteins or polypeptides are well known in the art, e.g., U.S. Pat. No. 4,518,584, incorporated herein by reference, which techniques are also described in further detail herein. Such modifications include the deletion, insertion or substitution of bases, and thus, changes in the amino acid sequence. Changes may be made to increase the cytokine activity of a protein, to increase its biological stability or half-life, to change its glycosylation pattern, and the like. All such modifications to the nucleotide sequences are encompassed by this invention.

2.8.1 Calcium-binding Proteolipid-Encoding DNA Segments

The present invention, in a general and overall sense, also concerns the isolation and characterization of a novel C. matruchotii calcium-binding proteolipid gene which encodes the apoprotein portion of the 10 kDa proteolipid isolated from C. matruchotii . A preferred embodiment of the present invention is a purified nucleic acid segment that encodes a protein that has at least a partial amino acid sequence in accordance with SEQ ID NO:1. Another embodiment of the present invention is a purified nucleic acid segment, further defined as including a nucleotide sequence in accordance with SEQ ID NO:3.

In a more preferred embodiment the purified nucleic acid segment consists essentially of the nucleotide sequence of SEQ ID NO:3 its complement and the degenerate variants thereof. As used herein, the term "nucleic acid segment" and "DNA segment" are used interchangeably and refer to a DNA molecule which has been isolated free of total genomic DNA of a particular species. Therefore, a "purified" DNA or nucleic acid segment as used herein, refers to a DNA segment which contains a calcium-binding proteolipid coding sequence yet is isolated away from, or purified free from, total genomic DNA, for example, total cDNA or human genomic DNA. Included within the term "DNA segment", are DNA segments and smaller fragments of such segments, and also recombinant vectors, including, for example, plasmids, cosmids, phage, viruses, and the like.

Similarly, a DNA segment comprising an isolated or purified bcf gene refers to a DNA segment including calcium-binding proteolipid coding sequences isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences, cDNA sequences or combinations thereof. "Isolated substantially away from other coding sequences" means that the gene of interest forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences which encode a calcium-binding proteolipid gene, that includes within its amino acid sequence an amino acid sequence in accordance with SEQ ID NO:1. In other embodiments, the amino acid sequence included may be that of SEQ ID NO:2, SEQ ID NO:5, or SEQ ID NO:8. Moreover, in other particular embodiments, the invention concerns isolated DNA segments and recombinant vectors incorporating DNA sequences which encode a gene that includes within its amino acid sequence the amino acid sequence of a calcium-binding proteolipid gene corresponding to homologous genes in other species, particularly bacterial species related to C. matruchotii.

Another preferred embodiment of the present invention is a purified nucleic acid segment that encodes a protein in accordance with SEQ ID NO:3, further defined as a recombinant vector. As used herein the term, "recombinant vector", refers to a vector that has been modified to contain a nucleic acid segment that encodes a calcium-binding proteolipid, or a fragment thereof. The recombinant vector may be further defined as an expression vector comprising a promoter operatively linked to said calcium-binding proteolipid-encoding nucleic acid segment.

A further preferred embodiment of the present invention is a host cell, made recombinant with a recombinant vector comprising a calcium binding protein encoding gene. The recombinant host cell may be a prokaryotic cell. In a more preferred embodiment, the recombinant host cell is a eukaryotic cell. As used herein, the term "engineered" or "recombinant" cell is intended to refer to a cell into which a recombinant gene, such as a gene encoding calcium-binding proteolipids, has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene (i.e., they will not contain introns), a copy of a genomic gene, or will include genes positioned adjacent to a promoter not naturally associated with the particular introduced gene.

Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. Howvever, the inventors do not exclude the possibility of employing a genomic version of a particular gene where desired.

In certain embodiments, the invention concerns isolated DNA segments and recombinant vectors which encode a protein or peptide that includes within its amino acid sequence an amino acid sequence essentially as set forth in SEQ ID NO:1 or in SEQ ID NO:2, SEQ ID NO:5 or SEQ ID NO:8. Naturally, where the DNA segment or vector encodes a full length bacteriocalcifin protein, or is intended for use in expressing the protein, the most preferred sequences are those which are essentially as set forth in SEQ ID NO:1 or SEQ ID NO:8. It is recognized that SEQ ID Nos:2,5 and 6 represent partial amino acid sequences at the N-terminus of the apoproteins comprising the protein-lipid complex isolated from *C. matruchotii* but which however are encoded by the isolated gene and as such are contemplated embodiments which also include up to the full length sequence of each apoprotein and functional variants as well.

The term "a sequence essentially as set forth in SEQ ID NO:1" or in reference to any other sequence referred to herein, means that the sequence substantially corresponds to a portion of SEQ ID NO:1 and has relatively few amino acids which are not identical to, or a biologically functional equivalent of, the amino acids of SEQ ID NO:1. The term "biologically functional equivalent" is well understood in the art and is further defined in detail herein, as a gene having a sequence essentially as set forth in SEQ ID NO:3, and that is associated with a calcium-binding proteolipid. Accordingly, sequences which have between about 70% and about 80%; or more preferably, between about 81% and about 90%; or even more preferably, between about 91%, 95% and about 99%; of amino acids which are identical or functionally equivalent to the amino acids of SEQ ID NO:1 will be sequences which are "essentially as set forth in SEQ ID NO:1"

In certain other embodiments, the invention concerns isolated DNA segments and recombinant vectors that include within their sequence a nucleic acid sequence essentially as set forth in SEQ ID NO:3. The term "essentially as set forth in SEQ ID NO:3," is used in the same sense as described above and means that the nucleic acid sequence substantially corresponds to a portion of SEQ ID NO:3, and has relatively few codons which are not identical, or functionally equivalent, to the codons of SEQ ID NO:3. The term "functionally equivalent codon" is used herein to refer to codons that encode the same amino acid, such as the six codons for arginine or serine, as set forth in Table 1, and also refers to codons that encode biologically equivalent amino acids.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences which may, for example, include various non-coding sequences flanking either of the 5' or 3' portions of the coding region or may include various internal sequences, i.e., introns, which are known to occur within genes.

Excepting intronic or flanking regions, and allowing for the degeneracy of the genetic code, sequences which have between about 70% and about 80%; or more preferably, between about 80% and about 90%; or even more preferably, between about 90% and about 99%; of nucleotides which are identical to the nucleotides of SEQ ID NO:3 will be sequences which are "essentially as set forth in SEQ ID NO:3". Sequences which arc essentially the same as those set forth in SEQ ID NO:3 may also be functionally defined as sequences which are capable of hybridizing to a nucleic acid segment containing the complement of SEQ ID NO:3 under relatively stringent conditions. Suitable relatively stringent hybridization conditions will be well known to those of skill in the art and are clearly set forth herein, for example conditions for use with Southern and Northern blot analysis, and as described in examples herein set forth.

Naturally, the present invention also encompasses DNA segments which are complementary, or essentially complementary, to the sequence set forth in SEQ ID NO:3. Nucleic acid sequences which are "complementary" are those which are capable of base-pairing according to the standard Watson-Crick complementarity rules. As used herein, the term "complementary sequences" means nucleic acid sequences which are substantially complementary, as may be assessed by the same nucleotide comparison set forth above, or as defined as being capable of hybridizing to the nucleic acid segment of SEQ ID NO:3 under relatively stringent conditions that may also be understood as including conditions of high stringency.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared which include a short stretch complementary to SEQ ID NO:3, such as about 10 to 15 or 20, 30, or 40 or so nucleotides, and which are up to 200 or so base pairs in length. DNA segments with total lengths of about 500, 200, 100 and about 50 base pairs in length are also contemplated to be useful.

A preferred embodiment of the present invention is a nucleic acid segment which comprises at least a 14-nucleotide long stretch which corresponds to, or is complementary to, the nucleic acid sequence of SEQ ID NO:3. In a more preferred embodiment the nucleic acid is further defined as comprising at least a 20 nucleotide long stretch, a 30 nucleotide long stretch, 50 nucleotide long stretch, 100 nucleotide long stretch, or at least a 200 nucleotide long stretch which corresponds to, or is complementary to, the nucleic acid sequence of SEQ ID NO:3. The nucleic acid segment may be further defined as having the nucleic acid sequence of SEQ ID NO:3.

A related embodiment of the present invention is a nucleic acid segment which comprises at least a 14-nucleotide long stretch which corresponds to, or is complementary to, the nucleic acid sequence of SEQ ID NO:3, further defined as comprising a nucleic acid fragment of up to 10,000 basepairs in length. A more preferred embodiment if a nucleic acid fragment comprising from 14 nucleotides of SEQ ID NO:3 up to 5,000 basepairs in length, 3,000 basepairs in length, 1,000 basepairs in length, 500 basepairs in length, or 100 basepairs in length.

Naturally, it will also be understood that this invention is not limited to the particular nucleic acid and amino acid sequences of SEQ ID NO:3. Recombinant vectors and isolated DNA segments may therefore variously include the calcium-binding proteolipid coding regions themselves, coding regions bearing selected alterations or modifications in the basic coding region, or they may encode larger polypeptides which nevertheless include calcium-binding proteolipid-coding regions or may encode biologically functional equivalent proteins or peptides which have variant amino acids sequences.

The DNA segments of the present invention encompass biologically functional equivalent calcium-binding proteins and peptides. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the calcium-binding proteolipids or to test mutants in order to examine activity or determine the presence of calcium-binding proteolipids in various cells and tissues at the molecular level.

A preferred embodiment of the present invention is a purified composition comprising a polypeptide having an amino acid sequence in accordance with any of SEQ ID Nos:1, 2, 5,6,or 7. The term "purified" as used herein, is intended to refer to a calcium-binding proteolipid composition, wherein the lipoprotein or any of the apoprotein components is purified to any degree relative to its naturally-obtainable state, i.e., in this case, relative to its purity within a eukaryotic cell extract. A preferred cell for the isolation of the proteins is a bacterial cell, such as *C. matruchotii* and related species; however, the proteolipid might also be isolated from patient specimens, recombinant cells, tissues, isolated subpopulations of tissues, and the like, as will be known to those of skill in the art, in light of the present disclosure. A purified calcium-binding proteolipid composition therefore also refers to a polypeptide having the amino acid sequence of SEQ ID NO:1 or SEQ ID NO:8 free from the environment in which it may naturally occur.

If desired, one may also prepare fusion proteins and peptides, e.g., where the calcium-binding proteolipid coding regions are aligned within the same expression unit with other proteins or peptides having desired functions, such as for purification or immunodetection purposes (e.g., proteins which may be purified by affinity chromatography and enzyme label coding regions, respectively).

Turning to the expression of the calcium-binding proteolipid gene whether from cDNA based or genomic DNA, one may proceed to prepare an expression system for the recombinant preparation of any one or more of the apo proteins of the calcium-binding proteolipid. The engineering of DNA segment(s) for expression in a prokaryotic or eukaryotic system may be performed by techniques generally known to those of skill in recombinant expression. For example, one may prepare a fusion protein that combines GST (glutathione-S-transferase) with the protein of SEQ ID NO:1 or SEQ ID NO:8 or a sequence including any or all of the apoprotein sequences that may be included in a calcium-binding proteolipid fusion protein. This may be a convenient means of bacterial expression. However, it is believed that virtually any expression system may be employed in the expression of such calcium-binding proteolipids.

Another embodiment is a method of preparing a protein composition comprising growing recombinant host cell comprising a vector that encodes a protein which includes an amino acid sequence in accordance with SEQ ID NO:1, SEQ ID NO:2, SEQ ID NO:5 or SEQ ID 7, under conditions permitting nucleic acid expression and protein production followed by recovering the protein so produced. The host cell, conditions permitting nucleic acid expression, protein production and recovery, will be known to those of skill in the art, in light of the present disclosure of the encoding gene.

2.8.2 Gene Constructs and DNA Segments

As used herein, the terms "gene" and "DNA segment" are both used to refer to a DNA molecule that has been isolated free of total genomic DNA of a particular species. Therefore, a gene or DNA segment encoding a calcium-binding proteolipid refers to a DNA segment that contains sequences encoding a calcium-binding protelipid, but is isolated away from, or purified free from, total genomic DNA of the species from which the DNA is obtained. Included within the term "DNA segment", are DNA segments and smaller fragments of such segments, and also recombinant vectors, including, for example, plasmids, cosmids, phage, retroviruses, adenoviruses, and the like.

The term "gene" is used for simplicity to refer to a functional protein or peptide encoding unit. As will be understood by those in the art, this functional term includes both genomic sequences and cDNA sequences. "Isolated substantially away from other coding sequences" means that the gene of interest, in this case, a calcium-binding proteolipid gene, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions, such as sequences encoding leader peptides or targeting sequences, later added to the segment by the hand of man.

2.8.3 Recombinant Vectors Expressing Calcium-binding Proteolipid Protein

A particular aspect of this invention provides novel ways in which to utilize calcium-binding proteolipid-encoding DNA segments and recombinant vectors comprising DNA segments encoding the component proteins of the proteolipid. As is well known to those of skill in the art, many such vectors are readily available. One particular detailed example of a suitable vector for expression in mammalian cells is that described in U.S. Pat. No. 5,168,050, incorporated herein by reference. However, there is no requirement that a highly purified vector be used, so long as the coding segment employed encodes a calcium-binding protein and does not include any coding or regulatory sequences that would have an adverse effect on cells. Therefore, it will also be understood that useful nucleic acid sequences may include additional residues, such as additional non-coding sequences flanking either of the 5' or 3' portions of the coding region or may include various internal sequences, i.e., introns, which are known to occur within genes.

After identifying an appropriate calcium-binding proteolipid-encoding gene or DNA molecule, it may be inserted into any one of the many vectors currently known in the art, so that it will direct the expression and production of the calcium-binding protein when incorporated into a host cell. In a recombinant expression vector, the coding portion of the DNA segment is positioned under the control of a promoter. The promoter may be in the form of the promoter which is naturally associated with a calcium-binding protein-encoding gene, as may be obtained by isolating the 5' non-coding sequences located upstream of the coding segment or exon, for example, using recombinant cloning and/or PCR technology, in connection with the compositions disclosed herein.

In certain embodiments, it is contemplated that particular advantages will be gained by positioning the bacteriocalcifin-encoding DNA segment under the control of a recombinant, or heterologous, promoter. As used herein, a recombinant or heterologous promoter is intended to refer to a promoter that is not normally associated with a calcium-binding proteolipid gene in its natural environment. Such promoters may include those normally associated with other calcium-binding polypeptide genes, and/or promoters isolated from any other bacterial, viral, eukaryotic, or mammalian cell. Naturally, it will be important to employ a promoter that effectively directs the expression of the DNA segment in the particular cell containing the vector comprising the calcium-binding protein gene.

The use of recombinant promoters to achieve protein expression is generally known to those of skill in the art of molecular biology, for example, see Sambrook et al., (1989). The promoters employed may be constitutive, or inducible, and can be used under the appropriate conditions to direct high level or regulated expression of the introduced DNA segment. The currently preferred promoters are those such as CMV, RSV LTR, the SV40 promoter alone, and the SV40 promoter in combination with the SV40 enhancer.

2.9 Methods of DNA Transfection

Technology for introduction of DNA into cells is well-known to those of skill in the art. Four general methods for delivering a gene into cells have been described: (1) chemical methods (Graham and Van der Eb, 1973); (2) physical methods such as microinjection (Capecchi, 1980), electroporation (Wong and Neumann, 1982; Fromm et al., 1985) and the gene gun (Yang et al., 1990); (3) viral vectors (Clapp, 1993; Danos and Heard, 1992; Eglitis and Anderson, 1988); and (4) receptor-mediated mechanisms (Wu et al., 1991; Curiel et al., 1991; Wagner et al., 1992).

2.9.1 Liposomes and Nanocapsules

The formation and use of liposomes is generally known to those of skill in the art (see for example, Couvreur et al., 1991 which describes the use of liposomes and nanocapsules in the targeted antibiotic therapy of intracellular bacterial infections and diseases). Recently, liposomes were developed with improved serum stability and circulation half-times (Gabizon and Papahadjopoulos, 1988; Allen and Chourn, 1987). The following is a brief description of these DNA delivery modes.

Nanocapsules can generally entrap compounds in a stable and reproducible way (Henry-Michelland et al., 1987). To avoid side effects due to intracellular polymeric overloading, such ultrafine particles (sized around 0.1 $\mu$m) should be designed using polymers able to be degraded in vivo. Biodegradable polyalkyl-cyanoacrylate nanoparticles that meet these requirements are contemplated for use in the present invention, and such particles may be easily made, as described (Couvreur et al., 1984; 1988).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 $\mu$m. Sonication of MLVs results in the formation of small unilamellar vesicles (SUVs) with diameters in the range of 200 to 500 Å, containing an aqueous solution in the core.

In addition to the teachings of Couvreur et al. (1991), the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

2.10 Expression of Calcium-binding Protein

For the expression of calcium-binding protein, once a suitable (full-length if desired) clone or clones have been obtained, whether they be cDNA based or genomic, one may proceed to prepare an expression system for the recombinant preparation of calcium-binding protein. The engineering of DNA segment(s) for expression in a prokaryotic or eukaryotic system may be performed by techniques generally known to those of skill in recombinant expression. It is believed that virtually any expression system may be employed in the expression of calcium-binding protein.

Calcium-binding proteolipids may be successfully expressed in eukaryotic expression systems, however, it is also envisioned that bacterial expression systems may be used for the preparation of bacteriocalcifin proteins for virtually all purposes. The cDNA for bacteriocalcifin protein may be separately expressed in bacterial systems, with the encoded proteins being expressed as fusions with β-galactosidase, ubiquitin, *Schistosoma japonicum* glutathione S-transferase, green fluorescent protein and the like. It is believed that bacterial expression will ultimately have advantages over eukaryotic expression in terms of ease of use and quantity of materials obtained thereby.

It is proposed that transformation of host cells with DNA segments encoding bacteriocalcifins will provide a convenient means for obtaining calcium-binding proteins and peptides. Both cDNA and genomic sequences are suitable for eukaryotic expression, as the host cell will, of course, process the genomic transcripts to yield functional mRNA for translation into protein.

It is similarly believed that almost any eukaryotic expression system may be utilized for the expression of calcium-binding protein, e.g., baculovirus-based, glutamine synthase-based or dihydrofolate reductase-based systems could be employed. However, in preferred embodiments, it is contemplated that plasmid vectors incorporating an origin of replication and an efficient eukaryotic promoter, as exemplified by the eukaryotic vectors of the pCMV series, such as pCMV5, will be of most use.

For expression in this manner, one would position the coding sequences adjacent to and under the control of the promoter. It is understood in the art that to bring a coding sequence under the control of such a promoter, one positions the 5' end of the transcription initiation site of the transcriptional reading frame of the protein between about 1 and about 50 nucleotides "downstream" of (i.e., 3' of) the chosen promoter.

Where eukaryotic expression is contemplated, one will also typically desire to incorporate into the transcriptional unit which includes calcium-binding protein, an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

Translational enhancers may also be incorporated as part of the vector DNA. Thus the DNA constructs of the present invention should also preferable contain one or more 5' non-translated leader sequences which may serve to enhance expression of the gene products from the resulting mRNA transcripts. Such sequences may be derived from the promoter selected to express the gene or can be specifically modified to increase translation of the RNA. Such regions may also be obtained from viral RNAs, from suitable eukaryotic genes, or from a synthetic gene sequence (Griffiths, et al, 1993).

Such "enhancer" sequences may be desirable to increase or alter the translational efficiency of the resultant mRNA. The present invention is not limited to constructs where the enhancer is derived from the native 5'-nontranslated promoter sequence, but may also include non-translated leader sequences derived from other non-related promoters such as other enhancer transcriptional activators or genes.

It is contemplated that virtually any of the commonly employed host cells can be used in connection with the expression of calcium-binding protein in accordance herewith. Examples include cell lines typically employed for eukaryotic expression such as 239, AtT-20, HepG2, VERO, HeLa, CHO, WI 38, BHK, COS-7, RIN and MDCK cell lines.

It is contemplated that calcium-binding protein may be "overexpressed", i.e., expressed in increased levels relative to its natural expression in human cells, or even relative to the expression of other proteins in a recombinant host cell containing calcium-binding protein-encoding DNA segments. Such overexpression may be assessed by a variety of methods, including radio-labeling and/or protein purification. However, simple and direct methods are preferred, for example, those involving SDS/PAGE and protein staining or Western blotting, followed by quantitative analyses, such as densitometric scanning of the resultant gel or blot. A specific increase in the level of the recombinant protein or peptide in comparison to the level in natural calcium-binding protein-producing animal cells is indicative of overexpression, as is a relative abundance of the specific protein in relation to the other proteins produced by the host cell and, e.g., visible on a gel.

As used herein, the term "engineered" or "recombinant" cell is intended to refer to a cell into which a recombinant gene, such as a gene encoding a calcium-binding peptide has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene (i.e., they will not contain introns), a copy of a genomic gene, or will include genes positioned adjacent to a promoter not naturally associated with the particular introduced gene.

It will be understood that recombinant calcium-binding protein may differ from naturally produced calcium-binding protein in certain ways. In particular, the degree of post-translational modifications, such as, for example, glycosylation and phosphorylation may be different between the recombinant calcium-binding protein and the calcium binding polypeptide purified from a natural source, such as calcifying bacteria.

Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventors do not exclude the possibility of employing a genomic version of a particular gene where desired.

After identifying an appropriate DNA molecule by any or a combination of means as described above, the DNA may then be inserted into any one of the many vectors currently known in the art and transferred to a prokaryotic or eukaryotic host cell where it will direct the expression and production of the so-called "recombinant" version of the protein. The recombinant host cell may be selected from a group consisting of S. mutans, E. coli, S. cerevisae. Bacillus sp., Lactococci sp., Enterococci sp., or Salmonella sp. In certain preferred embodiments, the recombinant host cell will have a recA phenotype.

Where the introduction of a recombinant version of one or more of the foregoing genes is required, it will be important to introduce the gene such that it is under the control of a promoter that effectively directs the expression of the gene in the cell type chosen for engineering. In general, one will desire to employ a promoter that allows constitutive (constant) expression of the gene of interest. Commonly used constitutive promoters are generally viral in origin, and include the cytomegalovirus (CMV) promoter, the Rous sarcoma long-terminal repeat (LTR) sequence, and the SV40 early gene promoter. The use of these constitutive promoters will ensure a high, constant level of expression of the introduced genes. The level of expression from the introduced genes of interest can vary in different clones, probably as a function of the site of insertion of the recombinant gene in the chromosomal DNA. Thus, the level of expression of a particular recombinant gene can be chosen by evaluating different clones derived from each transfection experiment; once that line is chosen, the constitutive promoter ensures that the desired level of expression is permanently maintained. It may also be possible to use promoters that are specific for cell type used for engineering, such as the insulin promoter in insulinoma cell lines, or the prolactin or growth hormone promoters in anterior pituitary cell lines.

2.10.1 Enhanced Production of Calcium-binding Protein

One of the problems with calcium-binding proteins isolated from natural sources is low yields and extensive purification processes. An aspect of the present invention is the enhanced production of calcium-binding protein by recombinant methodologies in a bacterial host, employing DNA constructs to transform Gram-positive or Gram-negative bacterial cells. For example, the use of *Escherichia coli* expression systems is well known to those of skill in the art, as is the use of other bacterial species such as *Bacillus subtilis* or *Streptococcus sanguis*.

Further aspects of the invention include high expression vectors incorporating DNA encoding the novel bacteriocalcifin and its variants. It is contemplated that vectors providing enhanced expression of bacteriocalcifin in other systems such as *S. mutans* will also be obtainable. Where it is desirable, modifications of the physical properties of bacteriocalcifin may be sought to increase its solubility or expression in liquid culture. The bcf locus may be placed under control of a high expression promoter or the components of the expression system altered to enhance expression.

In further embodiments, the DNA encoding the bacteriocalcifin of the present invention allows for the large scale production and isolation of the bacteriocalcifin polypeptide. This can be accomplished by directing the expression of the mutacin polhpeptide by cloning the DNA encoding the bacteriocalcifin polypeptide into a suitable expression vector. Such an expression vector may then be transformed into a host cell that is able to produce the bacteriocalcifin protein. The bacteriocalcifin protein may then be purified, e.g., by means provided for in this disclosure and utilized in a biologically active form. Non-biologically active recombinant bacteriocalcifin may also have utility, e.g., as an immunogen to prepare anti-bacteriocalcifin antibodies.

2.10.3 Cloning of Calcium-binding Protein Gene

In still another embodiment, the present disclosure provides methods for cloning the DNA encoding the calcium-binding polypeptide. Using methods well known to those of skill in the art, the DNA that encodes the purified calcium-binding protein of the present invention may be isolated and purified. For example, by designing a degenerate oligonucleotide comprising nucleotides complementary to the DNA encoding sequence of SEQ ID NO:1 or SEQ ID NO:8, the calcium-binding protein-encoding DNA can be cloned from a *C. matruchotii* cell library. Such sequences have been designed based on the N-terminal sequences of these sequences, i.e., SEQ ID NO:9, SEQ ID NO:10, SEQ ID NO:11 and SEQ ID NO:12.

The DNA sequences disclosed by the invention allow for the preparation of relatively short DNA (or RNA) sequences which have the ability to specifically hybridize to a gene encoding the calcium-binding polypeptides. Such a gene, is here termed the bcf gene and is understood to mean the gene locus encoding the calcium-binding proteolipid protein structural gene. In these aspects, nucleic acid probes of an appropriate length are prepared. Such probes are typically prespred based on the consideration of the defined amino acid sequence of purified calcium-binding protein. The ability of such nucleic acid probes to specifically hybridize to cbp gene sequences lend them particular utility in a variety of embodiments. For example, the probes may be used in a variety of diagnostic assays for detecting the presence of cbp genes in oral mucosal samples; however, other uses are envisioned, including identification of bcf gene sequences encoding similar or mutant polypeptides related to the bacteriocalcifin. Other uses include the use of mutant species primers, or primers to prepare other genetic constructs.

A first step in such cloning procedures is the screening of an appropriate DNA library, such as, in the present case, genomic or cDNA prepared from an appropriate cell library; for example, *C. matruchotii* cells. The screening procedure may be an expression screening protocol employing antibodies directed against the protein, or activity assays. Alternatively, screening may be based on the hybridization of oligonucleotide probes, designed from a consideration of portions of the amino acid sequence of the protein, or from the DNA sequences of genes encoding related proteins. Another cloning approach contemplated to be particularly suitable is the use of a probe or primer directed to a gene known to be generally associated with, e.g., within the same operon as, the structural gene that one desires to clone.

Another approach toward identifying the gene(s) responsible for the production of calcium-binding protein is to locate genes known to be adjacent to related calcium-binding protein genes. From sequenced loci in genes that encode similarly functional peptides, it will be possible to determine if these genes share areas of common sequences. A series of oligonucleotide primers complementary to conserved sequences could be used in PCR reactions to amplify the intervening sequence, this amplicon could be used as a probe to identify putative bacteriocalcifin genes. PCR technology is described in U.S. Pat. No. 4,603,102, incorporated herein by reference. Where such a bacteriocalcifin gene is found to be part of every known calcium-binding protein gene, the structural gene for calcium-binding protein should be nearby and readily identified by a technique known as "chromosome walking".

Antibodies against the proteolipid from *C. matruchotii* have immunologically detected the presence of proteolipid in calcified heart valves. Antibodies against the bacterial proteolipids may play a role as therapeutic agents in the detection, treatment and prevention of bacterial endocarditis and calcification of bicuspid heart valves.

A proteolipid from *Corynebacterium matruchotii* has calcification activity and a molecular weight of less than 10 kilodaltons. The present invention provides biologically active proteolipids comprising the amino acids sequences of bacteriocalcifin-1 (SEQ ID NO:1) and bacteriocalcifin-2 (SEQ ID NO:2), as well as the nucleotide sequence of the gene for the 5.5 kilodalton proteolipid of (SEQ ID NO:3) Among the biological properties of the proteolipids in the present invention is the capability to induce the formation of hydroxyapatite in vivo, in vitro from a metastable calcium phosphate solution, and the binding of calcium in an in vitro assay.

The purification is a process comprising culturing *C. matruchotii* in medium comprising calcium; extracting proteolipid from the cultured *C. matruchotii* cells with a chloroform:methanol mixture; precipitating the proteolipid from the chloroform:methanol extract with acetone and/or diethyl ether; and hydrophobic interaction chromatography on SEPHADEX™ LH-20 using chloroform:methanol as the mobile phase. This proteolipid comprises a protein with an N-terminal amino acid sequence of Ala-Gly-Val-Pro-Gly-Val (SEQ ID NO:4). The proteolipid has a more extensive N-terminal amino acid sequence of (SEQ ID NO:2).

The proteolipid preparation comprises, after delipidation, delipidated proteolipids (apoproteins) having molecular weights of about 7.5 kilodaltons, about 5.5 kilodaltons, and about 5.0 kilodaltons as determined by sodium dodecyl sulfate polyacrylamide gel electrophoresis (SDS-PAGE). The 7.5 kilodalton apoprotein component of the *C. matruchotii* 10 kilodalton proteolipid preparation has an N-terminal amino acid sequence of (SEQ ID NO:2).

The 5.5 kilodalton apoprotein has an N-terminal amino acid sequence of (SEQ ID NO:5). The 5.5 kilodalton apoprotein component of the 10 kilodalton *C. matruchotii* proteolipid preparation has a sequence of 50 amino acids (SEQ ID NO:1).

The 5.0 kilodalton apoprotein has an N-terminal amino acid sequence of (SEQ ID NO:5). The 5.0 kilodalton apoprotein component of the 10 kilodalton C. matruchotii proteolipid preparation has a sequence of 47 amino acids (SEQ ID NO:8).

The invention also comprises the cDNA nucleotide sequence for the 5.5 kilodalton apoprotein and any other nucleotide gene sequence that contains the nucleotide sequence for the gene of the 5.5 kilodalton apoprotein, as well as any of the oligonucleotide primers, based on the amino acid sequence of the 5.5 kilodalton aproproteolipid, used to generate these sequences by use of PCR™ technique. The 5.5 kilodalton apoprotein has a nucleotide sequence of (SEQ ID NO:3).

Also part of the present invention are polyclonal and monoclonal antibodies directed against the 10 kilodalton proteolipid preparation of C. matruchotii, as well as the use of these polyclonal and monoclonal antibodies diagnostically and therapeutically. The antibodies of the present invention are useful in detecting the presence of C. matruchotii and other calcifying microorganism, such as, but not limited to, Escherichia coli strains and Streptococcus sanguis, that produce substantially homologous proteolipids that are involved in calcification and can specifically be detected by the before-mentioned antibodies. The polyclonal and monoclonal antibodies are also useful in inhibiting the formation of dental calculus and calcification of heart valves. A method of the present invention is for inhibiting dental calculus and heart valve calcification and comprises inducing immunity to the 10 kilodalton proteolipid preparation of C. matruchotii.

The present invention also provides compositions, such as diagnostic, therapeutical, and pharmaceutical compositions, containing the proteolipid preparation or any of its apoprotein components of the present invention as well as antibodies against the proteolipid preparation of the present invention and methods of using either the proteolipid and/or the antibodies in treatment and diagnosis.

Other and further objects features and advantages will be apparent from the following description of the presently preferred embodiments of the invention, given for the purposes of disclosure when taken in conjunction with the accompanying drawings.

3.0 BRIEF DESCRIPTION OF THE DRAWINGS

FIG. 1 Calcium binding of C. matruchotii proteolipid before and after delipidation. The proteolipid was extracted and purified from bacteria that had been cultured for 4 days and lyophilized. The purified proteolipid (25 µg protein) was then assayed for calcium binding activity without any additional treatment, after treatment with hydroxylamine, or after chromatography on SEPHADEX™ LH-20 and treatment with hydroxylamine as described in Example 1. Chloroform:methanol (2:1, v/v) was used as a negative control. Activity was expressed as a percentage of the calcium found in the untreated samples which was arbitrarily set at 100%. All values are the mean ±SEM of 3 independent samples. *P<0.05, treated vs. untreated control.

Figure 2:
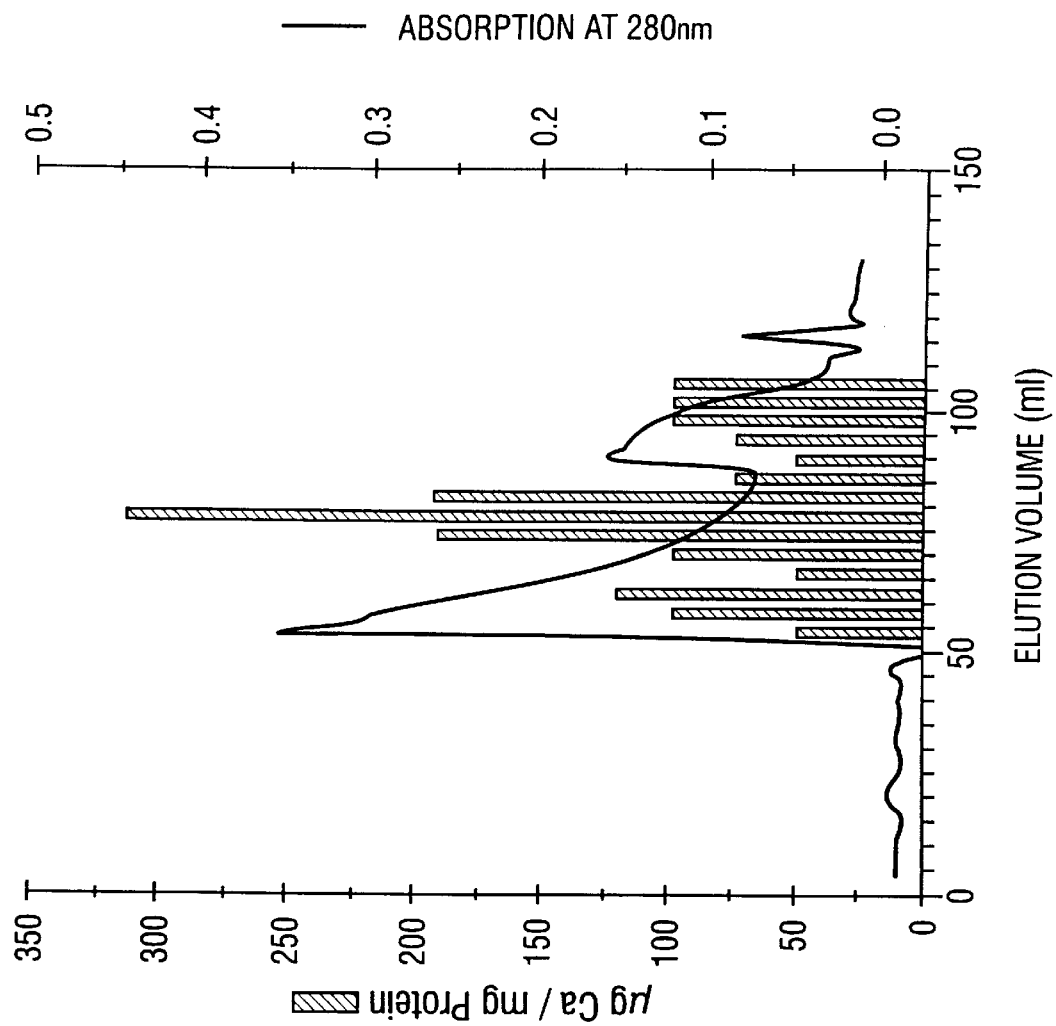

FIG. 2 Chromatography of C. matruchotii proteolipid extract on SEPHADEX™ LH-20. Proteolipid was extracted from bacteria that had been cultured for 4 days and lyophilized. Four mg of partially purified proteolipid protein were loaded onto a SEPHADEX™ LH-20 column (2.5×25 cm) that had been equilibrated in chloroform:methanol (2:1, v/v). The column was eluted at a flow rate of 0.5 ml/min and 2 ml fractions were collected. Absorbance at 280 nm was measured for all fractions. All fractions were assayed for in vitro calcium binding activity.

Figure 3:
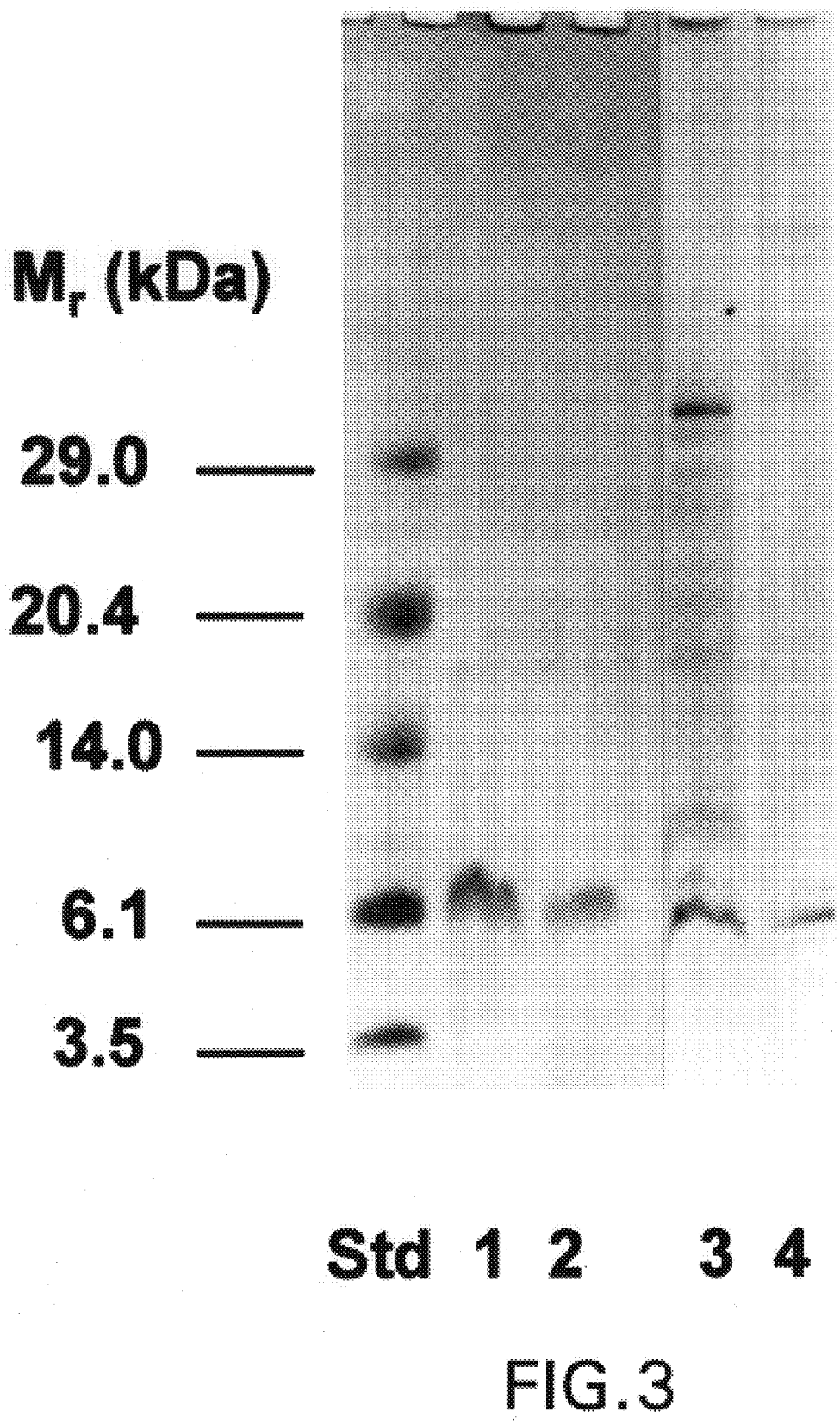

FIG. 3. SDS-PAGE of proteolipid before and after chromatography on SEPHADEX™ LH-20. Proteolipid was extracted from bacteria that had been cultured for 4 days and lyophilized. The proteolipid was isolated by salt extraction and ether precipitation as described in Example 1, followed by chromatography on SEPHADEX™ LH-20. Samples were electrophoresed on SDS-PAA gels in Tris-tricine buffer and stained with Coomassie Brilliant Blue followed by silver stain. Std: Molecular weight markers; Lanes 1 and 3: Proteolipid extract stained with Coomassie (lane 1) or silver (lane 3); Lanes 2 and 4: Proteolipid extract after chromatography on SEPHADEX™ LH-20 stained with Coomassie (lane 2) or silver (lane 4).

Figure 4:
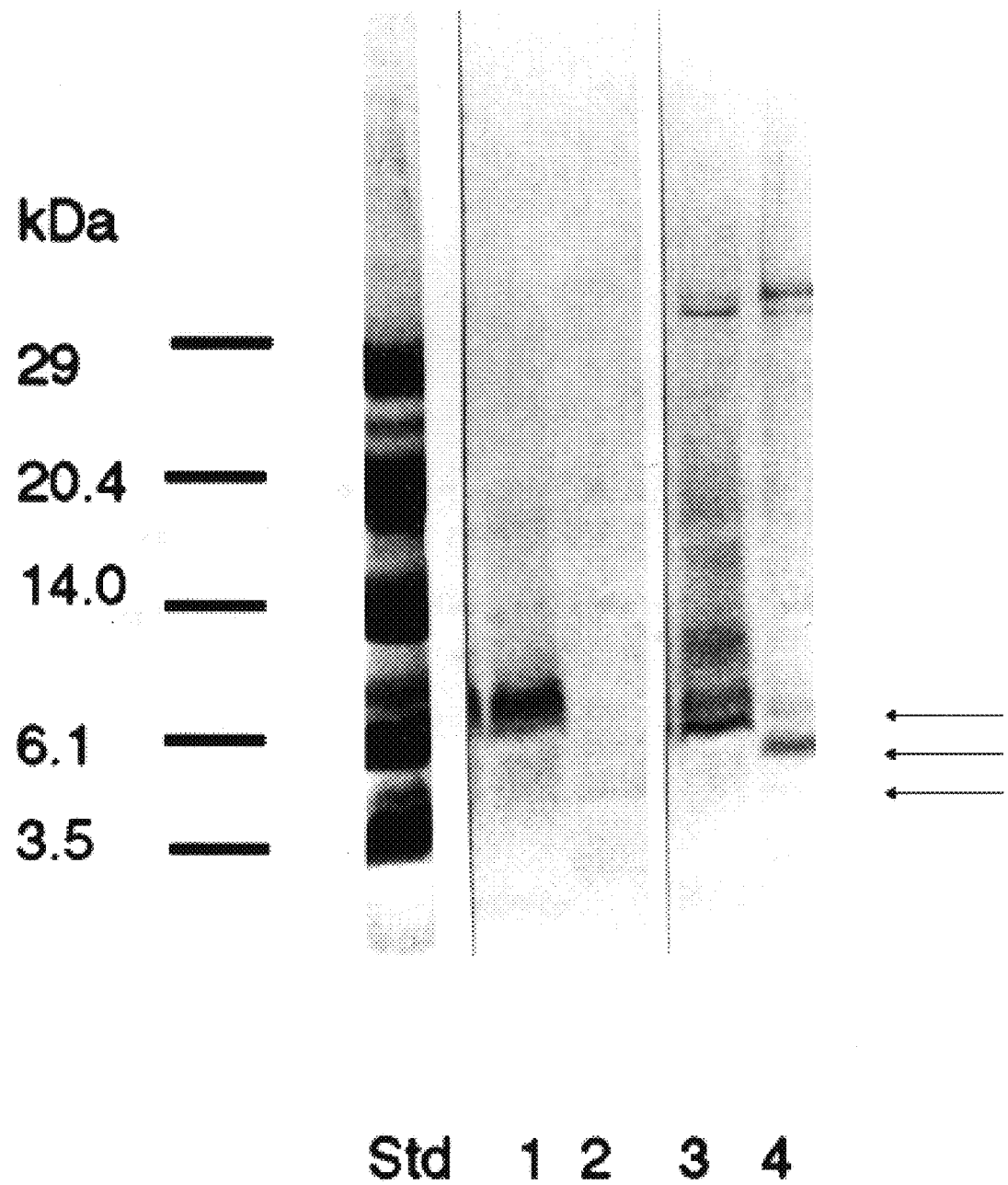

FIG. 4. SDS-PAGE of proteolipid before and after treatment with methanolic KOH. Proteolipid was extracted from bacteria that had been cultured for 4 days and lyophilized. The proteolipid was extracted as described in Example 1, followed by treatment with methanolic KOH. Samples were subjected to electrophoresis on SDS-PAA gels in Tris-tricine buffer and stained with Coomassie Brilliant Blue followed by silver stain. Std: Molecular weight markers; Lanes 1 and 3: Proteolipid extract, stained with Coomassie (lane 1) or silver (lane 3); Lanes 2 and 4: Proteolipid extract after treatment with methanol-KOH, stained with Coomassie (lane 2) or silver (lane 4).

FIG. 5. N-terminal amino acid sequence of the 10 kilodalton proteolipid preparation and the 7.5 kDa apoprotein of C. matruchotii. Proteolipid was extracted from bacteria that had been cultured for 4 days and lyophilized. The proteolipid was isolated by salt extraction and ether precipitation as described in Example 1, followed by treatment with methanolic KOH. Samples were electrophoresed on SDS-PAA gels in Tris-tricine buffer, followed by electrophoretic transfer to ProBlott membrane, staining with Coomassie Brilliant Blue and subsequent amino acid sequencing of the stained protein bands. Ser(P): phosphoserine residue.

FIG. 6. Amino acid sequence of the C. matruchotii proteolipid extract. Proteolipid was extracted from bacteria that had been cultured for 4 days and lyophilized. The proteolipid was isolated by salt extraction and ether precipitation as described in Example 1, followed by treatment with methanolic KOH and CNBr. Samples were electrophoresed on SDS-PAA gels in Tris-tricine buffer, followed by electrophoretic transfer to ProBlott membrane and staining with Coomassie Brilliant Blue. Stained protein bands were cut out and the amino acid sequence determined A: Amino acid sequence of the 5.5 kDa proteolipid. B: Amino acid sequence of the 5.0 kDa proteolipid. (Met) is the assumed N-terminus of the proteolipid protein core (see text). Underlined: homology with human and porcine phosphoprotein phosphatase 2A (Hemming et al., 1990). Box: potential phosphorylation site.

Figure 7:
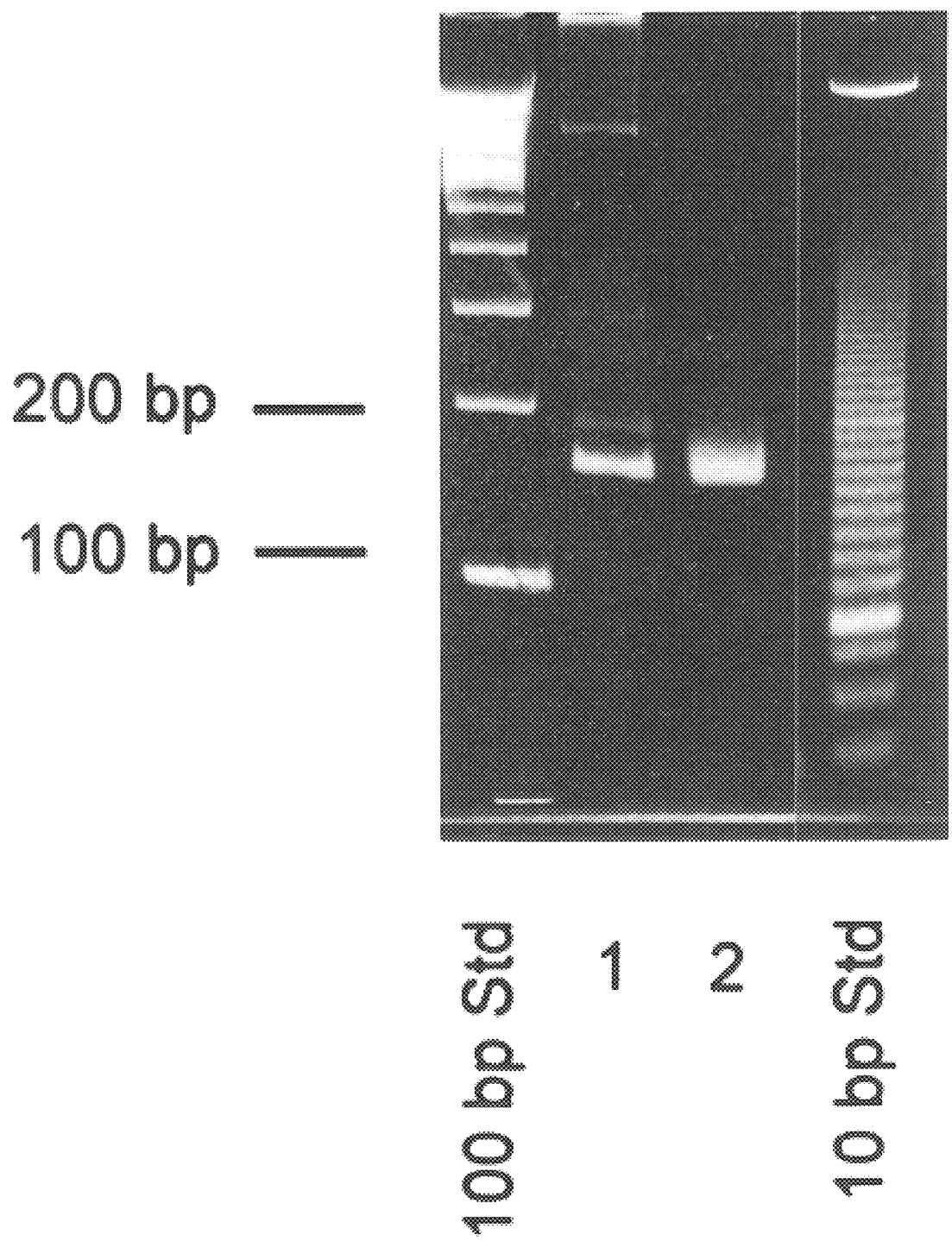

FIG. 7. Acrylamide gel electrophoresis of 5.5 kilodalton proteolipid cDNA. The 5.5 kilodalton proteolipid gene was amplified from C. matruchotii chromosomal DNA by PCR™ using oligonucleotide primers pp6-N5 (SEQ ID NO:9) and pp6-C5 (SEQ IDS NO:9) based on the amino acid sequence of the 5.5 kDa proteolipid. Typically, 30 PCR™ cycles were performed with an annealing temperature of 64° C. The PCR™ products were electrophoresed on a 10% acrylamide gel in Tris-borate-EDTA buffer, stained with ethidium bromide and visualized with UV-light. Lane 1: PCR™ products after 30 cycles at 64° C.; Lane 2:

Agarose-gel purified proteolipid cDNA. 100 bp Std: 100 basepair molecular size marker; 10 bp Std: 10 basepair molecular size marker.

FIG. 8. Nucleotide sequence of the 5.5 kDa proteolipid cDNA. The cDNA was obtained as described for FIG. 7. The sequence of the oligonucleotide primers is indicated above the nucleotide sequence. Primers contained the indicated 5'- and 3'-extensions (CG and GC) and additional restriction sites (EcoRI and BamHI).

Figure 9A:
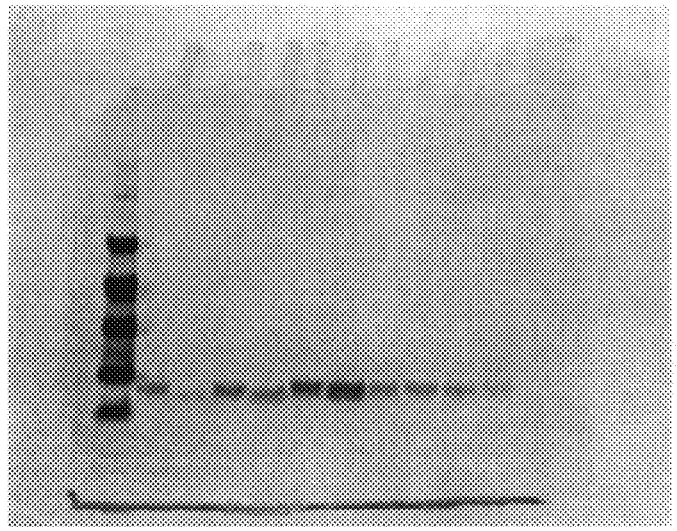
Figure 9B:
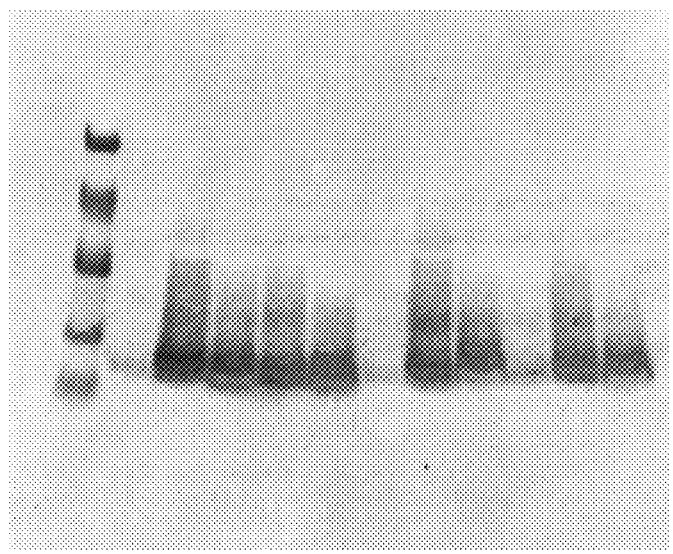
Figure 9C:
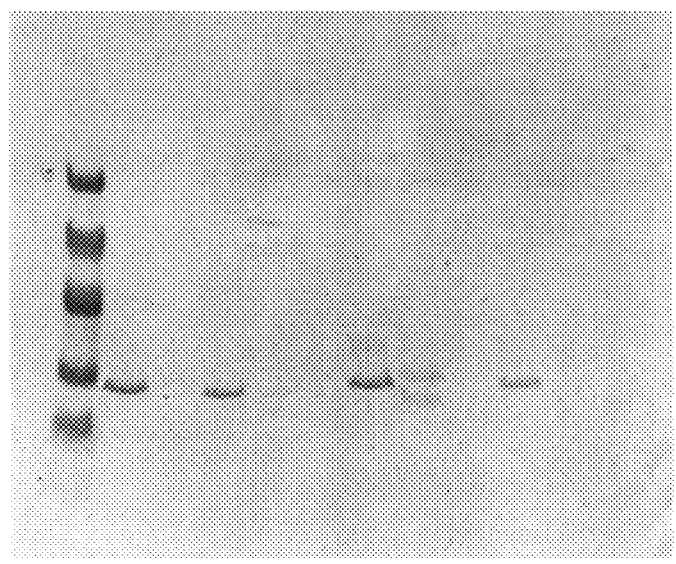

FIGS. 9A–C SDS-PAGE and Western blot of proteolipid. Proteolipid was extracted from bacteria that had been cultured for 4 days and lyophilized. The proteolipid was extracted as described in the Materials and Methods section. Samples were subjected to electrophoresis on SDS-PAA gels in Tris-tricine buffer, electroblotted to ProBlott membrane. Proteolipid was detected by immunostaining as described in the Materials and Methods section. Panel 9A: SDS-PAA gel, stained with ProBlue; Panel 9B: immunodetection with rabbit polyclonal antibody; Panel 9C: immunodetection with mouse monoclonal antibody.

Figure 10:
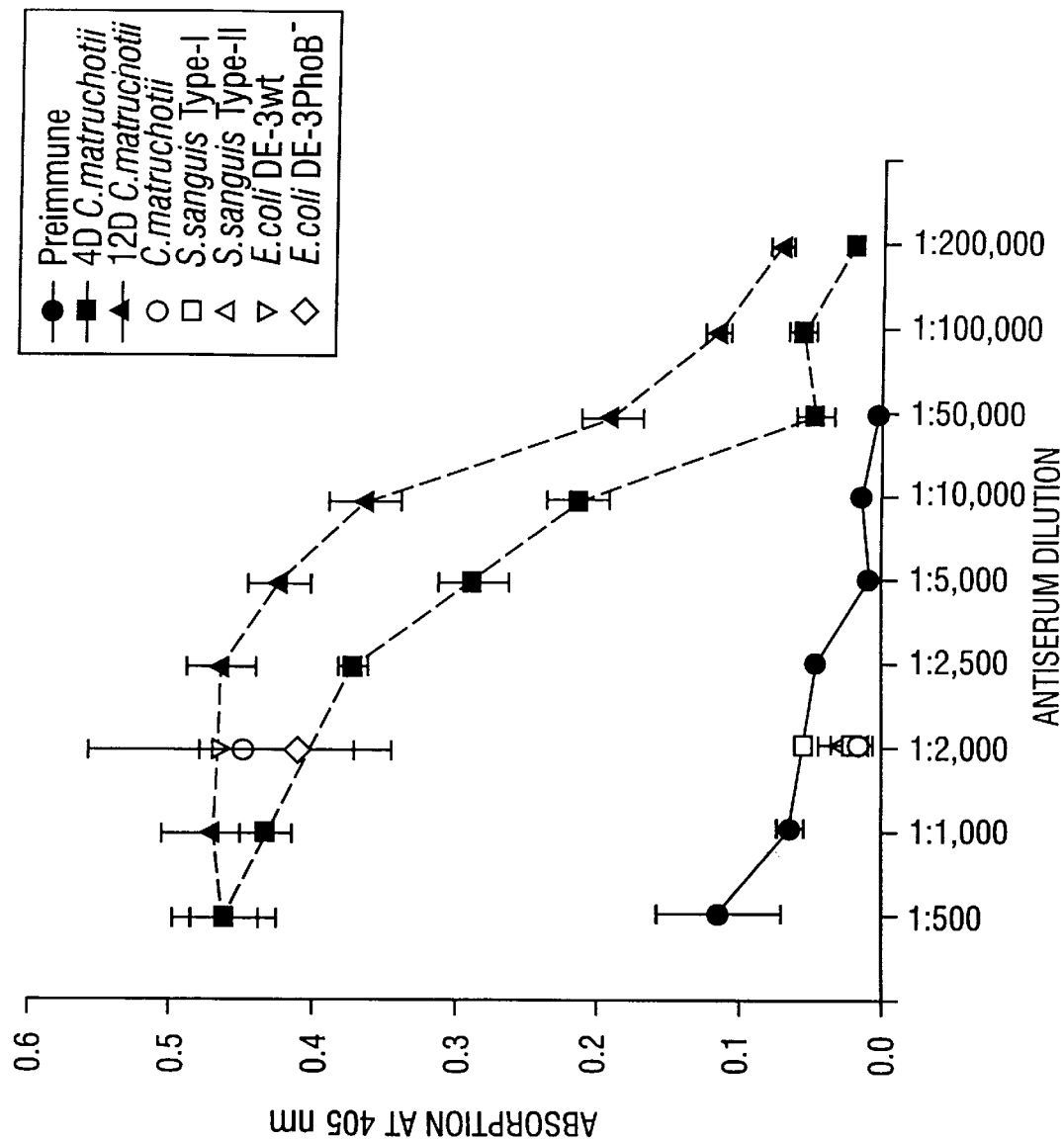

FIG. 10. ELISA assay of proteolipid-containing preparations with polyclonal antibody generated against 10 kilodalton proteolipid preparation of C. matruchotii. Primary antibody dilutions used are indicated. Preimmune: preimmune serum; 4D C. matruchotii: protelipid extracted from a 4 day culture; 12D C. matruchotii: protelipid extracted from a 12 day culture; C. matruchotii: membrane preparation from a 4 day culture; S. sanguis Type-I and S. sanguis Type-II: proteolipid extract from Streptococcus sanguis Type-I and Streptococcus Type-II; E. coli DE-3 wt: Escherichia coli DE-3 wildtype; E. coli DE-3 PhoB⁻: Escherichia coli DE-3 PhoB⁻ mutant.

4.0 DETAILED DESCRIPTION OF ILLUSTRATIVE EMBODIMENTS

4.1 ELISAs

ELISAs may be used in conjunction with the invention. In an ELISA assay, proteins or peptides incorporating calcium binding proteolipids or proteins are immobilized onto a selected surface, preferably a surface exhibiting a protein affinity such as the wells of a polystyrene microtiter plate. After washing to remove incompletely adsorbed material, it is desirable to bind or coat the assay plate wells with a nonspecific protein that is known to be antigenically neutral with regard to the test antisera such as bovine serum albumin (BSA), casein or solutions of powdered milk. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 hr, at temperatures preferably on the order of about 25° to about 27° C. Following incubation, the antisera-contacted surface is washed so as to remove non-immunocomplexed material. A preferred washing procedure includes washing with a solution such as PBS/Tween®, or borate buffer.

Following formation of specific immunocomplexes between the test sample and the bound antigen, and subsequent washing, the occurrence and even amount of immunocomplex formation may be determined by subjecting same to a second antibody having specificity for the first. To provide a detecting means, the second antibody will preferably have an associated enzyme that will generate a color development upon incubating with an appropriate chromogenic substrate. Thus, for example, one will desire to contact and incubate the antisera-bound surface with a urease-conjugated, peroxidase-conjugated or alkaline phosphatase-conjugated anti-rabbit, anti-mouse or anti-human IgG for a period of time and under conditions which favor the development of immunocomplex formation (e.g., incubation for 2 hr at room temperature in a PBS-containing solution such as PBS/Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase, or 5-bromo-4-chloro-3-indoyl phosphate (BCIP) and nitroblue tetrazolium (NBT) in the case of alkaline phosphatase as the enzyme label. Quantitation is then achieved by measuring the degree of color generation, e.g., using a visible spectrum spectrophotometer.

4.2 Epitopic Core Sequences

The present invention is also directed to protein or peptide compositions, free from total cells and other peptides, which comprise a purified protein or peptide which incorporates an epitope that is immunologically cross-reactive with one or more anti-calcium binding proteolipids or calcium binding protein antibodies.

As used herein, the term "incorporating an epitope(s) that is immunologically cross-reactive with one or more anti-calcium binding proteolipid or calcium binding protein antibodies" is intended to refer to a peptide or protein antigen which includes a primary, secondary or tertiary structure similar to an epitope located within a calcium binding polypeptide. The level of similarity will generally be to such a degree that monoclonal or polyclonal antibodies directed against the calcium binding polypeptide will also bind to, react with, or otherwise recognize, the cross-reactive peptide or protein antigen. Various immunoassay methods may be employed in conjunction with such antibodies, such as, for example, Western blotting, ELISA, RIA, and the like, all of which are known to those of skill in the art.

The identification of calcium binding epitopes, and/or their functional equivalents, suitable for use in vaccines is a relatively straightforward matter. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, for example, Jameson and Wolf, 1988; Wolf et al., 1988; U.S. Pat. Nos. 4,554,101). The amino acid sequence of these "epitopic core sequences" may then be readily incorporated into peptides, either through the application of peptide synthesis or recombinant technology.

Preferred peptides for use in accordance with the present invention will generally be on the order of about 5 to about 25 amino acids in length, and more preferably about 8 to about 20 amino acids in length. It is proposed that shorter antigenic calcium binding protein-derived peptide sequences will provide advantages in certain circumstances, for example, in the preparation of vaccines or in immunologic detection assays. Exemplary advantages include the ease of preparation and purification, the relatively low cost and improved reproducibility of production, and advantageous biodistribution.

It is proposed that particular advantages of the present invention may be realized through the preparation of synthetic peptides which include modified and/or extended epitopic/immunogenic core sequences which result in a "universal" epitopic peptide directed to calcium binding protein and calcium binding protein-related sequences. It is proposed that these regions represent those which are most likely to promote T-cell or B-cell stimulation in an animal, and, hence, elicit specific antibody production in such an animal.

An epitopic core sequence, as used herein, is a relatively short stretch of amino acids that is "complementary" to, and therefore will bind, antigen binding sites on calcium-binding protein antibodies. Additionally or alternatively, an epitopic core sequence is one that will elicit antibodies that are cross-reactive with antibodies directed against the peptide compositions of the present invention. It will be understood that in the context of the present disclosure, the term "complementary" refers to amino acids or peptides that exhibit an attractive force towards each other. Thus, certain epitope core sequences of the present invention may be operationally defined in terms of their ability to compete with or perhaps displace the binding of the desired protein antigen with the corresponding protein-directed antisera.

In general, the size of the polypeptide antigen is not believed to be particularly crucial, so long as it is at least large enough to carry the identified core sequence or sequences. The smallest useful core sequence anticipated by the present disclosure would generally be on the order of about 5 amino acids in length, with sequences on the order of 8 or 25 being more preferred. Thus, this size will generally correspond to the smallest peptide antigens prepared in accordance with the invention. However, the size of the antigen may be larger where desired, so long as it contains a basic epitopic core sequence.

The identification of epitopic core sequences is known to those of skill in the art, for example, as described in U.S. Pat. No. 4,554,101, incorporated herein by reference, which teaches the identification and preparation of epitopes from amino acid sequences on the basis of hydrophilicity. Moreover, numerous computer programs are available for use in predicting antigenic portions of proteins (see e.g., Jameson and Wolf, 1988; Wolf el al., 1988). Computerized peptide sequence analysis programs (e.g., DNAStar® software, DNAStar, Inc., Madison, Wis.) may also be useful in designing synthetic calcium binding peptides and peptide analogs in accordance with the present disclosure.

Syntheses of epitopic sequences, or peptides which include an antigenic epitope within their sequence, are readily achieved using conventional synthetic techniques such as the solid phase method (e.g., through the use of commercially available peptide synthesizer such as an Applied Biosystems Model 430A Peptide Synthesizer). Peptide antigens synthesized in this manner may then be aliquoted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of about 7.0 to about 7.5. Moreover, it may be desirable to include agents which will inhibit microbial growth, such as sodium azide or Merthiolate. For extended storage in an aqueous state it will be desirable to store the solutions at 4° C., or more preferably, frozen. Of course, where the peptides are stored in a lyophilized or powdered state, they may be stored virtually indefinitely, e.g., in metered aliquots that may be rehydrated with a predetermined amount of water (preferably distilled) or buffer prior to use.

4.3 Immunoprecipitation

The antibodies of the present invention are particularly useful for the isolation of antigens by immunoprecipitation. Immunoprecipitation involves the separation of the target antigen component from a complex mixture, and is used to discriminate or isolate minute amounts of protein. For the isolation of membrane proteins cells must be solubilized into detergent micelles. Nonionic salts are preferred, since other agents such as bile salts, precipitate at acid pH or in the presence of bivalent cations.

In an alternative embodiment the antibodies of the present invention are useful for the close juxtaposition of two antigens. This is particularly useful for increasing the localized concentration of antigens, e.g., enzyme-substrate pairs.

4.4 Western Blots

The compositions of the present invention will find great use in immunoblot or Western blot analysis. The anti-calcium binding protein antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. This is especially useful when the antigens studied are immunoglobulins (precluding the use of immunoglobulins binding bacterial cell wall components), the antigens studied cross-react with the detecting agent, or they migrate at the same relative molecular weight as a cross-reacting signal.

Immunologically-based detection methods for use in conjunction with Western blotting including enzymatically-, radiolabel-, or fluorescently-tagged secondary antibodies against the proteolipid are considered to be of particular use in this regard.

4.5 Vaccines

The present invention contemplates vaccines for use in both active and passive immunization embodiments. Immunogenic compositions, proposed to be suitable for use as a vaccine, may be prepared most readily directly from immunogenic calcium binding peptides prepared in a manner disclosed herein. Preferably the antigenic material is extensively dialyzed to remove undesired small molecular weight molecules and/or lyophilized for more ready formulation into a desired vehicle.

The preparation of vaccines which contain calcium binding peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables. Either as liquid solutions or suspensions: solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccines.

Vaccines may be conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of about 0.5% to about 10%, preferably about 1 to about 2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10 to about 95% of active ingredient, preferably about 25 to about 70%.

The calcium binding protein-derived peptides of the present invention may be formulated into the vaccine as neutral or salt forms. Pharmaceutically-acceptable salts, include the acid addition salts (formed with the free amino groups of the peptide) and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e.g., the capacity of the individual's immune system to synthesize antibodies, and the degree of protection desired. Precise amounts of active ingredient required to be administered depend on the judgment of the practitioner. However, suitable dosage ranges are of the order of several hundred micrograms active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the size of the host.

Various methods of achieving adjuvant effect for the vaccine includes use of agents such as aluminum hydroxide or phosphate (alum), commonly used as about 0.05 to about 0.1% solution in phosphate buffered saline, admixture with synthetic polymers of sugars (Carbopol®) used as an about 0.25% solution, aggregation of the protein in the vaccine by heat treatment with temperatures ranging between about 70° to about 101° C. for a 30-second to 2-minute period, respectively. Aggregation by reactivating with pepsin treated (Fab) antibodies to albumin, mixture with bacterial cells such as *C. parvum* or endotoxins or lipopolysaccharide components of Gram-negative bacteria, emulsion in physiologically acceptable oil vehicles such as mannide monooleate (Aracel A) or emulsion with a 20% solution of a perfluorocarbon (Fluosol-DA®) used as a block substitute may also be employed.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain protective levels of the antibodies. The course of the immunization may be followed by assays for antibodies for the supernatant antigens. The assays may be performed by labeling with conventional labels, such as radionuclides, enzymes, fluorescents, and the like. These techniques are well known and may be found in a wide variety of patents, such as U.S. Pat. Nos. 3,791,932; 4,174,384 and 3,949,064, as illustrative of these types of assays.

4.6 DNA Segments

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a DNA segment encoding a calcium binding peptide in its natural environment. Such promoters may include promoters normally associated with other genes, and/or promoters isolated from any viral, prokaryotic (e.g., bacterial), eukaryotic (e.g., fungal, yeast, plant, or animal) cell, and particularly those of mammalian cells. Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al., 1989. The promoters employed may be constitutive, or inducible, and can be used under the appropriate conditions to direct high level expression of the introduced DNA segment, such as is advantageous in the large-scale production of recombinant proteins or peptides. Appropriate promoter/expression systems contemplated for use in high-level expression include, but are not limited to, the Pichia expression vector system (Pharmacia LKB Biotechnology), a baculovirus system for expression in insect cells, or any suitable yeast or bacterial expression system.

In connection with expression embodiments to prepare recombinant proteins and peptides, it is contemplated that longer DNA segments will most often be used, with DNA segments encoding the entire peptide sequence being most preferred. However, it will be appreciated that the use of shorter DNA segments to direct the expression of calcium binding peptides or epitopic core regions, such as may be used to generate anti-calcium binding protein antibodies, also falls within the scope of the invention. DNA segments that encode calcium binding peptide antigens from about 10 to about 100 amino acids in length, or more preferably, from about 20 to about 80 amino acids in length, or even more preferably, from about 30 to about 70 amino acids in length are contemplated to be particularly useful.

In addition to their use in directing the expression of calcium binding peptides of the present invention, the nucleic acid sequences contemplated herein also have a variety of other uses. For example, they also have utility as probes or primers in nucleic acid hybridization embodiments. As such, it is contemplated that nucleic acid segments that comprise a sequence region that consists of at least an about 14-nucleotide long contiguous sequence that has the same sequence as, or is complementary to, an about 14-nucleotide long contiguous DNA segment of SEQ ID NO:3 will find particular utility. Longer contiguous identical or complementary sequences, e.g., those of about 20, 30, 40, 50, 100, 200, (including all intermediate lengths) and even those up to and including about 150-bp (full-length) sequences will also be of use in certain embodiments.

The ability of such nucleic acid probes to specifically hybridize to calcium binding protein-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of about 14, 15–20, 30, 40, 50, or even of about 100 to about 150 nucleotides or so, identical or complementary to the DNA sequence of SEQ ID NO:3, are particularly contemplated as hybridization probes for use in, e.g., Southern and Northern blotting. Smaller fragments will generally find use in hybridization embodiments, wherein the length of the contiguous complementary region may be varied, such as between about 10–14 and up to about 100 nucleotides, but larger contiguous complementarity stretches may be used, according to the length complementary sequences one wishes to detect.

The use of a hybridization probe of about 14 nucleotides in length allows the formation of a duplex molecule that is both stable and selective. Molecules having coiltiguous complementary sequences over stretches greater than 14 bases in length are generally preferred, though, in order to increase stability and selectivity of the hybrid, and thereby improve the quality and degree of specific hybrid molecules obtained. One will generally prefer to design nucleic acid molecules having gene-complementary stretches of about 15 to about 20 contiguous nucleotides, or even longer where desired.

Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as PCR, by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of prol)e towards target sequence. For applications requiring high selectivity, one will typically desire to employ relatively stringent conditions to form the hybrids, e.g., one will select relatively low salt and/or high temperature conditions, such as provided by about 0.02 M to about 0.15 M NaCl at temperatures of about 50° C. to about 70° C. Such selective conditions tolerate little, if any, mismatch between the probe and the template or target strand, and would be particularly suitable for isolating calcium binding protein-encoding DNA segments. Detection of DNA segments via hybridization is well-known to those of skill in the art, and the teachings of U.S. Pat. Nos. 4,965,188 and 5,176,995 (each incorporated herein by reference) are exemplary of the methods of hybridization analyses. Teachings such as those found in the texts of Maloy et al., 1994; Segal, 1976; Prokop, 1991; and Kuby, 1994, are particularly relevant.

Of course, for some applications, for example, where one desires to prepare mutants employing a mutant primer strand hybridized to an underlying template or where one seeks to isolate calcium binding protein-encoding sequences from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, calorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

4.7 Biological Functional Equivalents

Modification and changes may be made in the structure of the peptides of the present invention and DNA segments which encode them and still obtain a functional molecule that encodes a protein or peptide with desirable characteristics. The following is a discussion based upon changing the amino acids of a protein to create an equivalent, or even an improved, second-generation molecule. The amino acid changes may be achieved by changing the codons of the DNA sequence, according to the following codon table:

TABLE 1

| Amino Acids | | | Codons | | | |
|---|---|---|---|---|---|---|
| Alanine | Ala | A | GCA | GCC | GCG | GCU |
| Cysteine | Cys | C | UGC | UGU | | |
| Aspartic acid | Asp | D | GAC | GAU | | |
| Glutamic acid | Glu | E | GAA | GAG | | |
| Phenylalanine | Phe | F | UUC | UUU | | |
| Glycine | Gly | G | GGA | GGC | GGG | GGU |
| Histidine | His | H | CAC | CAU | | |
| Isoleucine | Ile | I | AUA | AUC | AUU | |
| Lysine | Lys | K | AAA | AAG | | |
| Leucine | Leu | L | UUA | UUG | CUA | CUC | CUG | CUU |
| Methionine | Met | M | AUG | | | |
| Asparagine | Asn | N | AAC | AAU | | |
| Proline | Pro | P | CCA | CCC | CCG | CCU |
| Glutamine | Gln | Q | CAA | CAG | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU |
| Valine | Val | V | GUA | GUC | GUG | GUU |
| Tryptophan | Trp | W | UGG | | | |
| Tyrosine | Tyr | Y | UAC | UAU | | |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

4.8 Site-Specific Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered. In the present work, preferred primers are exemplified by SEQ ID NO:9, SEQ ID NO:10, SEQ ID NO:11 and SEQ ID NO:12 representing from 26 to 36 nucleotides.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected peptide-encoding DNA segments using site-directed mutagenesis is provided as a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants.

4.9 Monoclonal Antibodies

Means for preparing and characterizing antibodies are well known in the art (See, e.g., Harlow and Lane, 1988; incorporated herein by reference).

The methods for generating monoclonal antibodies (mAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

mAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified calcium binding protein, polypeptide or peptide such as represented by SEQ ID NO:1, SEQ ID NO:2, SEQ ID NO:5 or SEQ ID NO:8. The immunizing composition is administered in a manner effective to stimulate antibody producing cells. Rodents such as mice and rats are preferred animals, however, the use of rabbit, sheep or frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, X63-Ag8.653, NS1/1.Ag4 1, Sp210-Ag14, FO, NSO/U, MPC-11, MPC11-X45-GTG 1.7 and S194/5XXO Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, by Gefter et al., (1977). The use of electrically induced fusion methods is also appropriate (Goding, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate Block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

4.10 Pharmaceutical Compositions

The pharmaceutical compositions disclosed herein may be orally administered, for example, with an inert diluent or with an assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus ny additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

The composition can be formulated in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

A peptide given orally in an unprotected form is subject to digestion of the peptide in the stomach and intestine which could cause large losses of activity. Neutralization of gastric contents with gastric acid secretory suppressants (e.g., Tagamet, Zantac or Pepcid) prevents gastric inactivation of oral digestive enzyme supplements (Regan, et al., 1977), and a similar protocol will protect orally-administered calcium binding protein formulations as well. Additional protective formulations could include enteric coating of microspheres that encapsulate the agent, such that the microspheres do not release their contents until they reach the duodenum. With these measures, it would be expected that 2–3 mg of calcium binding protein taken orally would result in about 1 mg reaching the duodenum. The oral dosage form of calcium binding protein, its active fragments, derivatives or analogs may be in any convenient administrable form such as a solution, suspension, tablet, capsule or others known to those of skill in the art.

5.0 EXAMPLES

5.1 Example 1

Isolation and Characterization of *C. matruchotii* Proteolipid

*Corynebacterium matruchotii* (ATCC #14266, American Type Culture Collection, Rockville, Md.) was cultured in Bacto® Brain Heart Infusion medium (Difco Laboratories, Detroit, Mich.) and grown aerobically at 37° C. without agitation for 4 days. The cells do not exhibit the ability to support in vitro calcification prior to this time (Boyan et al., 1992; Boyan-Salyers et al., 1978b). Cells were harvested by centrifugation at 10,000×g for 20 min at 4° C., washed with ultrapure water, re-centrifuged and lyophilized. The dry weight of the bacterial pellet was determined and the pellet was stored at −20° C. before extraction of the proteolipid.

Lyophilized bacteria (300 mg dry weight) were extracted in 200 ml chloroform:methanol (2:1, v/v, Burdick and Jackson HPLC grade, Baxter, Muskegon, Mich.) by gentle stirring overnight at 4° C. Remnant cell debris was removed by filtration through grade 50F and GF/F filters (Whatman, Hillsboro, Oreg.) and the organic extract washed overnight at 4° C. with 0.2 vol 0.1 M NaCl. The organic phase was collected, dried in a stream of $N_2$, and then redissolved in a small volume of chloroform:methanol (2:1, v/v). The crude proteolipid was precipitated overnight with 10 vol acetone at −20° C. and collected by centrifugation at 10,000×g for 30 min at 4° C. The pellet was redissolved in chloroform-:methanol as before and precipitated with 5 vol ice-cold diethyl ether. The pellet was recovered by centrifugation and resuspended in chloroform:methanol as before, and the tube purged with $N_2$ to prevent oxidation and stored at −80° C. Protein concentration was determined by a modification of the Lowry protein assay (Lees and Paxman 1972).

The proteolipid extract was further purified by column chromatography on SEPHADEX™ LH-20 (Pharmacia, Piscataway, N.J.) (bedvolume 2.5×25 cm) equilibrated in chloroform:methanol (2:1, v/v) (Ennever et al., 1976). Typically, 4–5 mg of proteolipid was dissolved to a final concentration of 1.25 mg protein/ml in chloroform:methanol (2:1, v/v), and loaded onto the column. The column was eluted with chloroform:methanol (2:1, v/v) at a flow rate of 0.5 ml/min. The optical density of the fractions was measured at 280 nm. Protein concentration of the fractions was determined by a modified Lowry protein assay (Lees and Paxman 1972). Fractions were purged with $N_2$ and stored at $-80°$ C.

Covalently attached fatty acids were removed from the proteolipid by mild treatment with 10 mM hydroxylamine in 100 mM Tris, pH 7.5, overnight at room temperature, which preferentially removes fatty acids covalently attached to serine residues (Magee and Schlesinger, 1982; McIlhinney, 1992), or more rigorously by treatment with 0.1 M KOH in anhydrous methanol for 2–4 hrs at 37° C. (McIlhinney, 1992). In both cases, deacylated proteolipid was recovered by centrifugation at 12,000×g for 15 min, washed twice with ether, redissolved in chloroform:methanol (2:1, v/v) and stored at $-80°$ C.

Sodium dodecyl sulfate polyacrylamide gel electrophoresis (SDS-PAGE) was performed according to the method of Schägger and Von Jagow (Schägger and Von Jagow, 1987) using precast 10–20% SDS-polyacrylamide (SDS-PAA) gels in Tris-tricine buffer (Integrated Separation Systems, Natick, Mass.). Proteolipid in chloroformn:methanol (2:1, v/v) was dried under $N_2$, dissolved in reducing SDS-PAGE sample loading buffer containing 0.4% SDS and 1% β-mercaptoethanol, and incubated for 30 min at 37° C. before electrophoresis (Laemmli, 1970). Prestained low molecular weight protein standards (3.5 kDa–29.0 kDa, Integrated Separation Systems, Natick, Mass.) were added to every gel. After electrophoresis proteins, were stained with the ISS Pro-Blue and Daiichi Silver Stain kits (Integrated Separation Systems, Natick, Mass.), adapted from previously described methods (Neuhoff et al., 1988; Ross and Peters, 1990).

SDS-polyacrylamide gradient gels in Tris-tricine buffer were required to achieve a satisfactory electrophoretic separation of the proteolipid, due to its hydrophobicity and low molecular weight. Under optimal conditions for separation, followed by staining with Coomassie Blue, the proteolipid migrated as a single, diffuse band having a molecular mass of 7–10 kDa (FIG. 3, lane 1). When the peak of activity eluting from the LH-20 column was electrophoresed on the same gel system, a similar diffuse protein band was observed (FIG. 3, lane 2). Staining the gels with silver revealed several additional minor proteins with higher molecular weights in the proteolipid extract (FIG. 3, lane 3), which were reduced after chromatography on SEPHADEX™ LH-20 (FIG. 3, lane 4).

Since hydroxylamine treatment of the proteolipid reduced the activity of the protein by 50%, a more vigorous delipidation technique was sought. When the proteolipid extract was treated with methanolic-KOH to completely remove covalently attached lipids, the relatively diffuse band at 7–10 kDa on SDS-PAGE was converted to three distinct bands with molecular mass of 5–7.5 kDa (FIG. 4).

Initial attempts at direct sequencing of the 10 kilodalton proteolipid preparations from C. matruchotii yielded a partial N-terminal amino acid sequence as shown in FIG. 5. After SDS-PAGE and electroblotting of the delipidated proteolipid preparation to ProBlott membrane, the 5.0 kilodalton to 7.5 kilodalton protein bands comprising the apoprotein preparation (FIG. 4, lanes 2 and 4), were sequenced. Only an amino acid sequence for the 7.5 kilodalton apoprotein could be obtained. The amino acid sequence was identical to the one obtained for the 10 kilodalton proteolipid preparation before treatment with methanolic KOH (FIG. 5), confirming that the 7.5 kilodalton protein is part of the 10 kilodalton proteolipid preparation. The amino acid sequence is unique and has not been reported before. Three phosphorylated Ser-residues are present at position 10, 13 and 25. No amino acid sequence could be obtained from the 5.5 kilodalton apoprotein and 5.0 kilodalton apoprotein, suggesting that the N-terminus of the protein was blocked.

Delipidation of purified proteolipid with methanolic KOH, followed by electrophoresis on SDS-PAA gels, blotting onto ProBlott membrane (Applied Biosystems, Foster City, Calif.), and sequencing of Coomassie Blue staining bands, yielded no amino acid sequence. It was necessary therefore to pretreat the proteolipid preparation with cyanogen bromide (CNBr) (Gross, 1967) to obtain an N-terminal amino acid sequence for the 5.5 kilodalton and 5.0 kilodalton components of the delipidated proteolipid preparation, After removal of lipids with methanolic KOH, proteolipid was treated by a modification of the CNBr-cleavage reaction described by Matsudaira (Matsudaira, 1990). Briefly, 100 μg of delipidated proteolipid was dried in a 1.7 ml microfuge tube by a stream of $N_2$, and dissolved in 100 μl 70% (v/v) formic acid. A few crystals of CNBr were added and dissolved by gentle vortexing. The tube was flushed with $N_2$, capped, sealed with Parafilm, wrapped in aluminum foil and incubated at room temperature for 15–18 hrs without agitation. The reaction was quenched by addition of 10 vol of distilled water, followed by lyophilization. The CNBr-treated proteolipid sample was dissolved in reducing SDS-PAGE sample buffer and electrophoresed on a 10–20% gradient SDS-polyacrylamide gel in Tris-tricine buffer in the presence of 0.1 mM sodium thioglycolate to prevent blocking of the amino-terminus (Yuen et al., 1988). Similarly, active fractions from the LH-20 column were pooled, treated with methanol-KOH, followed by cyanogen bromide treatment and SDS-PAGE. After electrophoresis, proteolipid was transferred to ProBlott membrane by electroblotting in 10 mM 3-(cyclohexylamino)-1-propanesulfonic acid (CAPS) buffer, pH 11.0, containing 10% (v/v) methanol (Matsudaira, 1987). The membrane was stained briefly with Coomassie Brilliant Blue R-250 (0.1% (w/v) in 40% (v/v) methanol, 1% (v/v) acetic acid) and protein bands of interest excised. Amino acid sequencing was performed on ABI 473A and ABI 477A automated amino acid sequencers (Applied Biosystems, Foster City, Calif.).

The complete amino acid sequence for the 5.0 and 5.5 kDa proteolipids was determined as described above (FIG. 6). The 5.5 kDa proteolipid consists of 50 amino acids, assuming that the CNBr treatment removed a Met residue from the N-terminus, and has a calculated molecular weight of 5354 and a isoelectric point (pI) of 4.28. The amino acid sequence of the 5.0 kDa protein is identical to the 5.5 kDa protein except for a truncation at the last 3 amino acids residues from the C-terminus. The resulting protein has a calculated molecular weight of 5067. Interestingly, the amino acid sequences contain a stretch of homology with human phosphoprotein phosphatase PP2A (Hemming et al., 1990) (FIG. 6, underlined segment). Both the 5.5 kDa protein and the 5.0 kDa protein contain a potential phosphorylation site at Ser[45]. No amino acids were observed beyond Thr[50] during the sequencing of the 5.5 kDa protein. Likewise, no amino acids beyond Leu[47] were found in the 5.0 kDa protein sequence. No amino acid sequence could be obtained from the 5.5 kilodalton apoprotein and 5.0 kilodalton apoprotein, suggesting that the N-terminus of the protein was blocked.

Western blot analysis using both polyclonal and monoclonal antibodies showed that the main protein band reacting with both poly- and monoclonal antibodies was the band around 8–10 kDa (FIG. 9). The polyclonal antibodies reacted with additional minor protein bands (Data not shown). Whether these proteins are contaminants or oligo- or multimeric forms of the proteolipid as suggested by Ennever and Swain (Ennever et al., 1978a; Swain et al., 1989) is not clear. However, aggregation of proteolipids, even under conditions employed for SDS-PAGE, is well documented (Blondin, 1979; Green et al., 1980; Lees et al., 1981).

Example 5.2

In Vitro Calcification Assay.

Proteolipid activity was determined by its ability to induce the precipitation of calcium phosphate from metastable synthetic lympH solution (1.35 mM $CaCl_2$, 0.40 mM $MgCl_2$, 0.25 mM $NaH_2PO_4$, 1.69 mM $Na_2HPO_4$, 0.024 mM Tris, and 117 mM NaCl at pH 7.4 (Boskey and Posner, 1982; Cuervo et al., 1973). The 10 kilodalton proteolipid was known to support calcium phosophate precipitation and further that the mineral phase that forms is hydroxyapatite (Boyan, 1985; Boyan et al., 1992; Boyan-Salyers and Boskey, 1980; Ennever et al., 1978a; Swain et al., 1989; Swain and Boyan, 1988).

Calcium binding, expressed as µg $Ca^{2+}$/mg protein, was used as an indicator of calcification, since the first step in the hydroxyapatite formation is the binding of calcium. Proteolipid (10–50 µg) in chloroform:methanol was dried in a microcentrifuge tube by a stream of $N_2$, suspended in 100 µl distilled water by vigorous vortexing for 1 minute, followed by incubation for 1 hr at 37° C. The sample was pelleted by centrifugation, resuspended in 1.5 ml synthetic lympH by vortexing and incubated for 7 days at 37° C. without agitation. Control tubes prepared by drying a comparable volume of chloroform:methanol (2:1, v/v) with $N_2$ were run with every assay. During the 7-day incubation, the pH (i.e.: 7.35–7.45) of the solution in the control tubes remained constant and no precipitation was observed, indicating that the solution remained metastable in the absence of nucleators. At the end of the incubation, tubes were centrifuged at 12,000×g for 10 min at 4° C. and the supernatants and any pellets analyzed for their calcium content by use of commercially available kits (Sigma Chemical Co., St. Louis, Mo.). Calcium content was expressed as µg calcium in the precipitate per mg proteolipid protein in the tube at the onset of the assay.

The proteolipid from C. matruchotii was capable of inducing in vitro calcium binding (FIG. 1, closed bar), based on its ability to precipitate $Ca^{2+}$ (144±20 µg/mg protein) from synthetic lymph. When proteolipid was treated with hydroxylamine prior to assay, a 50% loss of calcium binding activity was observed (FIG. 1, open bar). Following SEPHADEX™ LH-20 chromatography in vitro calcium binding activity eluted from the column in a relatively broad peak, suggesting heterogeneity in the sample (FIG. 2, hatched bars). The majority of the activity eluted at 74–84 ml (1.8–2.1 $V_o$) and was between two protein peaks, based on absorbance at 280 nm. A 50% reduction in calcium binding was observed after treatment of the SEPHADEX™ LH-20 fractions (74–84 ml $V_e$) with hydroxylamine (FIG. 1, hatched bar).

Example 5.3

Preparation of DNA from C. matruchotii.

A C. matruchotii total genomic DNA library was constructed in the pBK-CMV expression vector (STRATAGENE) and screened with labeled oligonucleotide probes generated by PCR™ with the oligonucleotide primers of SEQ ID NO:9 and SEQ ID NO:10 using techniques known to ones skilled in the art. Primers based on the preliminary amino acid sequence were designed to generate a cDNA probe, which was then used to screen the genomic library by use of the PCR™-technique. Positive clones were identified, subcloned in pBK-CMV and the resulting inserts were sequenced.

Chromosomal DNA was extracted from 1-liter cultures of C. matruchotii in Bacto® Brain Heart Infusion medium (Difco Laboratories, Detroit, Mich.) by a modification of the methods described by Moore (Moore, 1992). 4-Day cultures were harvested and bacterial pellets were resuspended in 18 ml 10 mM Tris-HCl, 1 mM ethylenediaminetetraacetic acid (EDTA), pH 7.6. To this suspension, 1 ml 10% SDS and 2 ml lysozyme (10 mg/ml in $H_2O$) were added, and the incubation continued on ice for 10 min. Twenty µl RNaseA (100 units/mg protein; 10 µg/µl in 10 mM Tris-HCl, pH 7.5, 15 mM NaCl; Sigma Chemical Co, St. Louis, Mo.) was added and the incubation continued for another 30 min at 37° C., followed by addition of 100 µl Proteinase K (20 units/mg; 20 mg/ml in $H_2O$; Bethesda Research Laboratories, Gaithersburg, Md.) and incubation for 1 hr at 37° C. After addition of 3.6 ml NaCl (5.0 M) and 3.0 ml 0.27 M cetyltrimethylammonium bromide, containing 0.7 M NaCl (CTAB/NaCl), the DNA was extracted twice with chloroform/isoamylalcohol (24:1, v/v), centrifuged for 10 min at 6,000×g, and the DNA precipitated with 0.6 vol ice-cold isopropanol. The precipitated DNA was dissolved in 2.5 ml 10 mM Tris-HCl, pH 7.5, containing 1 mM EDTA and stored at 4° C.

Oligonucleotide primers for the polymerase chain reaction (PCR™) were derived from the N-terminal amino acid sequence (SEQ ID :2) of the 7.5 kilodalton apoprotein (primers 2014A and 2014B) and the complete amino acid sequence (SEQ ID NO:1) of the 5.5 kDa apoprotein (primers pp6-N5 and pp6-C5) with the addition of restrictions sites to the 5'-end of each primer to facilitate cloning. Oligonucleotide primers were designed and synthesized based on the preferential codon usage reported for Colynebacteriunm species (Eikmanns, 1992; Malumbres et al., 1993).

TABLE 2

Oligonucleotide primers designed for PCR ™

Primer Nucleotide Sequence pp6-N5 5' CGGAATTCATGGAYTAYGGYCARATC 3' (SEQ ID NO:9)

pp6-C5 5' GCGGATCCRGTYTCRCCWAGYTCRGA 3' (SEQ ID NO:10)

TABLE 2-continued

Oligonucleotide primers designed for PCR™

Primer Nucleotide Sequence 2014A 5' CGGAATTCGCAGGCGTTCCAGGCGTTACCAAGAA 3' (SEQ ID NO:11)

2014B 5' GCGGATCCCTCGGACTTGGAGGAGCCGTCGCCAAC 3' (SEQ ID NO:12)

Oligonucleotide primers pp6-N5 and pp6-C5 correspond to the first 6 N-terminal amino acids and the C-terminal 6 amino acids of the 5.5 kDa proteolipid, respectively. Oligonucleotide primer 2014A and primer 2014B correspond to the amino acids 1–9 and amino acids 21–29 of the 7.5 kilodalton apoprotein, respectively. PCR™ reactions contained 10 mM Tris-HCl, pH 8.3, 50 mM KCl, 20 μM of each deoxynucleoside triphosphate, 2.5 mM MgCl$_2$, 20 pmol of each single-stranded primer, 10–100 ng of C. matruchotii chromosomal DNA, and 2.5 units of AmpliTaq DNA Polymerase (Perkin Elmer, Foster City, Calif.) in a total volume of 100 μl. After an initial denaturation step at 95° C. for 5 min, PCR™ amplification reactions were carried out for 30 cycles in a Perkin-Elmer Thermal Cycler 480 (Perkin Elmer, Foster City, Calif.) as follows: denaturation of template DNA at 95° C. for 1 min, primer annealing for 2 min at 64° C., followed by primer extension for 3 min at 72° C. The PCR™ products were analyzed on a 10% acrylamide gel in 45 mM Tris-borate, 1 mM EDTA, pH 7.8, followed by agarose-gel purification (Sambrook et al., 1989).

The cDNA was directly sequenced on an ABI 373A automated DNA sequencer (Applied Biosystems, Foster City, Calif.) using DNA-polymerase FS and the dye-terminal cycle sequencing technique (Perkin Elmer, Foster City, Calif.). Using the degenerate oligonucleotide primers pp6-N5 (SEQ ID NO:9) and pp6-C5 (SEQ ID NO:10), a cDNA preparation was obtained from the C. matruchotii chromosomal DNA by PCR™ that contained a major DNA fragment of approximately 166 basepairs (bp) in addition to several minor, larger DNA fragments (FIG. 7, lane 1). After agarose-gel purification of the major DNA fragment, only the 166 bp cDNA fragment was present in the preparation (FIG. 7, lane 2). The nucleotide sequence of the 166 bp cDNA corresponded to the 50 amino acids of the 5.5 kDa proteolipid and two 8 bp restriction linker sequences (SEQ ID NO:3, FIG. 8), thereby confirming the amino acid sequence of the 5.5 kDa proteolipid.

Example 5.4

Generation of Antibodies.

Antibodies against the C. matruchotii 10 kilodalton proteolipid preparation disclosed in Example 1 were generated by subcutaneous injection of 50–100 μg of proteolipid emulsified in Freund's adjuvant in rabbits, essentially as described in Reference (Harlow and Lane, 1988). Booster injections were given 3 weeks after the initial injections with 50–100 μg of proteolipid emulsified in Freund's incomplete adjuvans and bled from the ear vein. Polyclonal antiserum was purified by chromatography on Protein A-SEPHAROSE™ (Ey et al., 1978; Goding, 1978; Kessler, 1975; Lindmark et al., 1983). The titer of the antibodies was determined by an ELISA assay, essentially as described (Baker et al., 1982; Palfree and Elliot, 1982)

Monoclonal antibodies were generated in an antigen-free system (American Biogenetic Sciences, Notre Dame, Ind.). Supernatants from the mouse monoclonal cell lines were concentrated by spiral ultrafiltration, followed by affinity purification on immobilized Protein G, by methods known to ones skilled in the art (Akerstrom and Bjorck, 1986; Bennet et al., 1988). After dialysis against PBS, supernatants were stored at −80° C. The immunoreactivity was tested by an ELISA assay, essentially as described by Baker et al., (1982) or Palfree and Elliot, (1982).

After gel electrophoresis on 10–20% SDS-PAA gels in a Tris-tricine buffer system (Schägger and Von Jagow, 1987) proteins were electrophoretically transferred to ProBlott membranes (Applied Biosystems, Foster City, Calif.) in 10 mM CAPS (3-[cyclohexylamino]-1-propane sulfonic acid) pH 11, 10% methanol at 250 mA for 120 min at 4° C. (Matsudaira, 1987).

The incubation and detection methods employed are described by Harlow and Lane (1988) and are known to persons skilled in the art. After rinsing with H$_2$O, membranes were incubated in 5% non-fat dry milk in 25 mM Tris-HCl, 0.5 M NaCl, pH 7.5, to block non-specific binding. Blocked membranes were incubated with anti-proteolipid antibody (dilution for rabbit polyclonal antibody 1:1,000; dilution for mouse monoclonal antibody 1:500) in 25 mM Tris-HCl, 0.5 M NaCl, pH 7.5, for 1 hr at room temperature or overnight at 4° C., followed by three washes with 0.1% Triton X-100 in 25 mM Tris-HCl, 0.5 M NaCl, pH 7.5. Membranes were incubated with goat anti-rabbit or goat anti-mouse antibody, conjugated with alkaline phosphatase (Sigma, St. Louis, Mo.) in a 1:1,000 dilution in 25 mM Tris-HCl, 0.5 M NaCl, pH 7.5, for 90 min at room temperature. Membranes were washed three times with 0.1% Triton X-100 in 25 mM Tris-HCl, 0.5 M NaCl, pH 7.5, rinsed with H$_2$O, and briefly incubated in 0.1 M NaHCO$_3$, 1.0 mM MgCl$_2$, pH 9.8.

Antibody binding was visualized by incubating the membranes in 0.03% Nitro Blue Tetrazolium (NBT) and 0.015% 5-bromo-4-chloro-3-indoyl-phosphate (BCIP) (both from Sigma, St. Louis, Mo.) in 0.1 M NaHCO$_3$, 1.0 mM MgCl$_2$, pH 9.8, at room temperature. Color development was stopped by rinsing the membranes with H$_2$O.

Analysis of the 10 kilodalton proteolipid preparation from C. matruchotii in an ELISA showed a dose-dependent response (FIG. 10). Proteolipid extracted from C. matruchotii cultured for 4 days or 12 days before harvesting showed essentially an identical response in the ELISA. A lyophilized membrane preparation of C. matruchotii gave an identical response, confirming that the proteolipid from C. matruchotii is membrane-associated. Furthermore, the ELISA was capable of detecting calcifiable proteolipid in calcifying strains of E. coli DE-3 (wild type, and mutants PhoA⁻ and PhoB⁻), and in organic solvent extracts of membranes of the same bacteria, indicating substantial homology between the proteolipid preparation from C. matruchotii and E. coli. Proteolipid extracts from calcifying S. sanguis type II and non-calcifying S. sanguis type I did not show immunological cross-reactivity in the ELISA.

Example 5.5

Blocking of Mineralization by Polyclonal Antibodies.

Antibodies raised in rabbits against the neutral proteolipid fraction from *C. matruchotii* were capable of blocking in vitro mineralization (Boyan et al., 1992). A quantitative microassay was developed for testing calcium binding induced by bacteriocalcifin. The ability to form hydroxyapatite was confirmed by X-ray diffraction. The formation and deposition of hydroxyapatite was inhibited in a dose-dependent manner by the polyclonal antibodies (Boyan et al., 1992). mineralization by *S. mitis* and *S. sanguis* II, the calcifying variant of the oral bacterium *S. sanguis* I, was only partially inhibited by polyclonal antibodies, suggesting a difference in nucleation site or a difference in the antigenic determinants of the calcifiable proteolipid.

Example 5.6

Materials and Methods

Statistical Analysis. Data are presented as the mean ±SEM for the number of cultures or determinations shown in the figure or table legends. Differences between groups were determined by analysis of variance followed by the Student's t-test using Bonferonni's modification. P values<0.05 were considered significant.

DISCUSSION

The proteolipid purified and sequenced in the present invention was extracted in chloroform:methanol (2:1, v/v). However, the component apoproteins have molecular weights approximately one half that previously reported. This appears to be due in part to removal of noncovalently attached lipids via diethyl ether precipitation of the proteolipid. In order to achieve well separated bands by SDS-PAGE, it was necessary to further delipidate the proteolipid, removing bound lipid as well, thereby reducing the apparent molecular weights. The true molecular weight of the 5.5 kilodalton apoprotein, confirmed by the amino acid and nucleotide sequences, shows that the proteolipid isolated by chloroform:methanol (2:1, v/v) extraction, exists in its monomeric form with a molecular weight of 5354. The 5.0 kilodalton apoprotein, which has a C-terminal truncation of 3 amino acids, has an apparent molecular weight of 5067. It is possible that the higher molecular weight forms as reported by Ennever and Swain (Ennever et al., 1978a; Swain et al., 1989) may be analogous to the higher molecular weight forms of the calcium binding proteolipid shown in FIGS. 3 and 4. These higher molecular weight forms cross-react with the polyclonal antibodies raised against the 5.5 kilodalton apoprotein as shown in Western blots (FIG. 9). Such oligomers or multimers of the protein might be expected since aggregation of proteolipids is well documented (Blondin, 1979; Green et al., 1980; Lees et al., 1981).

Ennever and coworkers (Ennever et al., 1978a) have shown that disruption of the protein-phospholipid interaction following chromatography on SEPHADEX™ LH-20 in the presence of acidified chloroform:methanol results in loss of calcifiability of the proteolipid. Since this process disrupts the hydrophobic interactions between the protein and its associated phospholipids, it is probable that CPLX-formation is inhibited. It appears that covalently bound lipid is important for in vitro calcium binding activity as well. While the ability to precipitate calcium and phosphate was retained after diethylether extraction of the boundary phospholipids, this ability was partially lost following treatment of the proteolipid with hydroxylamine and completely removed following total delipidation with methanolic KOH. The relative contributions of the lipid moieties and the three-dimensional structure of the protein to the calcification process are yet to be determined.

Analysis of the amino acid sequence of the 5.5 kDa proteolipid reveals several interesting structural features. Assuming that Met is the N-terminal residue, the purified proteolipid has of 50 amino acids. The protein core has a molecular weight of 5354 and a pI of 4.28. The acidic pI indicates a high degree of secondary structure. Secondary structure predictions (Chou and Fasman, 1978; Rost and Sander, 1993) and hydrophobicity plots indicate that amino acid residues 4–22 could form a hydrophobic α-helix, potentially anchoring the protein in the membrane. To account for the extreme hydrophobicity of the protein, however, complex tertiary and/or quarternary structure is likely. Covalently bound lipid may contribute to the hydrophobic characteristics of the proteolipid.

The 5.5 kDa protein contains several hydroxyl-containing amino acids (Ser, Thr, Tyr) that would allow for O-acylation (Magee and Schlesinger, 1982). The Lys residues are potential N-acylation sites. However, no specific recognition sequences for myristoylation or palmitoylation are found (Magee and Schlesinger, 1982; McIlhinney, 1992; Turner, 1992). The amino acid sequence shows a short stretch of homology with the 65 kDa regulatory subunit of human and porcine phosphoprotein phosphatase 2A, a phosphatase involved in the modulation of phosphorylase B kinase, casein kinase 2 and MAP-2 kinase (Hemming et al., 1990). This homology may have functional significance for the role of the 5.5 kDa proteolipid in hydroxyapatite formation by *C. matruchotii*. The potential phosphorylation site at Ser$^{45}$ may play a role in the phosphatase activity as well as in transport of calcium and phosphate ions.

Analysis of the N-terminal amino acid sequence of the 7.5 kilodalton apoprotein shows the presence of 3 phosphorylated Ser-residues: Ser$^{10}$, Ser$^{13}$, and Ser$^{25}$. The phosphorylated amino acid residues may play a role in binding and transport of calcium and phosphate ions. This highly phosphorylated 7.5 kilodalton proteolipid is part of the proteolipid complex that is involved in the induction of apatite formation by regulation of phosphate and calcium binding and transport across the cellular membrane, thereby contributing to the conditions that favor the in vivo formation of hydroxyapatite. Previous studies have indicated that multiple proteolipids are present in *C. matruchotii*, at least two of which can function together to enhance H$^+$-tran port by bacteriorhodopsin-containing liposomes (Swain et al., 1989).

Data from ELISA assays indicate that the antibodies against the 10 kilodalton proteolipid preparation of *C. matruchotii* are capable of specifically binding and detecting proteolipid in proteolipid extracts and membrane fractions of *C. matruchotii*, and calcifying *E. coli* DE-3 (wild type, and mutants PhoA–, missing the alkaline phosphatase structural gene, and PhoB–, missing the alkaline phosphatase gene operon control clement)(FIG. 10). A calcifying strain of Streptococcus (*Streptococcus sanguis* type II) does not show cross-reactivity with the antibodies, indicating that the proteolipid in this strain does not have substantial homology with any of the apoprotein components of the *C. matruchotii* proteolipid preparation. The non-calcifying strain *S. sanguis* type I, which also lacks proteolipid (Boyan et al., 1992), does not cross-react with the antibodies either.

A proteolipid treated with methanolic KOH (McIlhinney, 1992) did not cross-react with monoclonal antibody in a Western blot, indicating that the monoclonal antibodies are specific for fully lipidated and therefore fully active calcifiable proteolipid. This provides a potentially powerful tool for screening for calcification activity in clinical bacterial cell isolates without the need for isolating proteolipid. The antibodies provide a selective tool to detect the presence of calcifiable proteolipid from *C. matruchotii* and other calcifying microorganisms that show substantial amino acid homology to the *C. matruchotii* proteolipid and/or its component proteins. Useful diagnosis may therefore be performed with such assays as Western immunoblot, ELISA and radioimmuno assay (RIA) to determine and quantify calcifying bacteria in pathologic dental calculus and heart valve calcification.

6.0 REFERENCES

Akerstrom and Bjorck, "A physicochemical study of protein G, a molecule with unique immunoglobulin G-binding properties," *Journal of Biological Chemistry*, 261:10240–7, 1986.

Anderson, "Vesicles associated with calcification in the matrix of epiphyseal cartilage," *Journal of Cell Biology*, 41:59–72, 1969.

Baker, Caterson, Christener, "Immunological characterization of cartilage proteoglycans,", *Methods in Enzymology*, 83:216–35, 1982.

Bennet, Hefeneider, Bakke, Merritt, Smith, Mourich, et al., "The production and characterization of murine monoclonal antibodies to a DNA receptor on human leukocytes," *Journal of Immunology*, 140:2937–42, 1988.

Blondin, "Resolution of the mitochondrial N,N'-dicyclohexylcarbodiimide binding proteolipid fraction into three similar sized proteins," *Biochemical and Biophysical Research Communications*, 87:1087–94, 1979.

Boskey and Posner, "Optimal conditions for a Ca-acidic phospholipid-$PO_4$ formation," *Calcified Tissue International*, 34:S1–7, 1982.

Boyan, Landis, Knight, Dereszewski, Zeagler, "Microbial hydroxyapatite formation as a model of proteolipid-dependent membrane-mediated calcification," *Scanning Electron Microscopy*, 4:1793–800, 1984.

Boyan, "Proteolipid-dependent calcification," In: 2nd International Conference on the Chemistry and Biology of mineralized Tissue, Butler W T, editor. Birmingham, Ala. EBSCO Media, pp. 125–31, 1985.

Boyan, Swain, Boskey "Mechanisms of microbial calcification," In: Recent Advances in the Study of Dental Calculus. Ten Cate J M, editor. Oxford: IRL Press, pp. 29–35, 1989a.

Boyan, Swain, Gomez, "Model for prokaryotic calcification," In: Origin, Evolution, and Modern Aspects of Biomineralization in Plants and Animals. Crick R E, editor. New York: Plenum Press, pp. 517–23, 1989.

Boyan, Swain, Everett, Schwartz, "Mechanisms of microbial mineralization," In: Calcification in Biological Systems. Bonucci E, editor. Boca Raton, Fla.: CRC Press, pp. 129–56, 1992.

Boyan and Boskey, "Co-isolation of proteolipids and calcium-phospholipid-phosphate complexes," *Calcified Tissue International* 36:214–8, 1984.

Boyan-Salyers, Vogel, Ennever, "Pre-apatitic mineral deposition in *Bacterionema matruchotii*," *Journal of Dental Research* 57:291–5, 1978a.

Boyan-Salyers, Vogel, Riggan, Summers, Howell, "Application of a microbial model to biologic calcification," *Metabolic Bone Disease and Related Research* 1:143–7, 1978b.

Boyan-Salyers and Boskey, "Relationship between proteolipids and calcium-phospholipid-phosphate complexes in *Bacterionema matruchotii* calcification," *Calcified Tissue International* 30:167–74, 1980.

Bulleid, "An experimental study of *Leptothrix buccalis*," *British Dental Journal*, 46:289–300, 1925.

Cao, Genge, Wu, Buzzi, Showman, Wuthier, "Characterization, cloning and expression of the 67-kDa annexin from chicken growth plate cartilage matrix vesicles," *Biochemical and Biophysical Research Communications* 197:556–61, 1993.

Chou and Fasman, "Prediction of the secondary structure of proteins from their amino acid sequence," *Advances in Enzymology and Related Areas of Molecular Biology* 47:45–148, 1978.

Cohen, Iakovidis, Brooks, Swain, Everett, Boyan, "Association of a calcifiable proteolipid with human bicuspid aortic valve calcification," *Circulation* 86: I-850, 1992.

Cuervo, Pita, Howell, "Inhibition of calcium phosphate mineral growth by proteoglycan aggregate fractions in a synthetic lymph," *Calcified Tissue Research* 13:1–10, 1973.

Debiec and Lorenc, "Identification of $Na^+,P_i$-binding protein in kidney and intestinal brush-border membranes," *Biochemical Journal*, 255:185–91, 1988.

Eikmanns, "Identification, sequence analysis, and expression of a *Corynebacterium glutamicum* gene cluster encoding the three glycolytic enzymes glyceraldehyDE-3-phosphate dehydrogenase, 3-phosphoglycerate kinase, and triosephosphate isomerase," *Journal of Bacteriology* 174:6076–86, 1992.

Ennever, "Intracellular calcification by oral filamentous microorganisms," *Journal of Periodontology*, 31:304–7, 1960.

Ennever, Vogel, Takazoe, "Calcium binding by a lipid extract of *Bacterioneina matruchotii*," *Calcified Tissue Research*, 2:296–8, 1968.

Ennever, Vogel, Streckfuss, "Synthetic medium for calcification of *Bacterionema matruchotii*," *Journal of Dental Research*, 50:1327–30, 1971.

Ennever, Vogel, Brown, Jr, "Survey of microorganisms for calcification in a synthetic medium," *Journal of Dental Research*, 51:1483–6, 1972.

Ennever, Vogel, Benson, "Lipid and calculus matrix calcification in vitro," *Journal of Dental Research*, 52:1056–9, 1973.

Ennever, Vogel, Streckfuss, "Calcification by *Escherichia coli*," *Journal of Bacteriology*, 119:1061–2, 1974.

Ennever, Vogel, Rider, Boyan-Salyers, "Nucleation of microbiologic calcification by proteolipid," *Proceedings of the Society for Experimental Biology and Medicine*, 152:147–50, 1976.

Ennever, Riggan, Vogel, Boyan-Salyers, "Characterization of *Bacterionema matruchotii* calcification nucleator," *Journal of Dental Research*, 57:637–42, 1978a.

Ennever, Vogel, Riggan, "Phospholipids of a bone matrix calcification nucleator," *Journal of Dental Research*, 57:731–4, 1978b.

Ennever, Vogel, Boyan-Salyers, Riggan, "Characterization of calculus matrix calcification nucleator," *Journal of Dental Research*, 58:619–23, 1979.

Everett and Hirschmann, "Transient bacteremia and endocarditis prophylaxis," *Medicine*, 56:61–77, 1977.

Ey, Prowse, Jenkin, "Isolation of pure $IgG_1$, $IgG_{2a}$, and $IgG_{2b}$ immunoglobulins from mouse serum using protein A-Sepharose," *Biochemistry*, 15:429–36, 1978.

Genge, Wu, Adkisson, I V, Wuthier, "Matrix vesicle annexins exhibit proteolipid-like properties. Selective partitioning into lipophilic solvents under acidic conditions," *Journal of Biological Chemistry*, 266:10678–85, 1991.

Genge, Cao, Wu, Buzzi, Showman, Arsenault, et al., "Establishment of the primary structure of the major lipid-dependent $Ca^{2+}$ binding proteins of chicken growth plate cartilage matrix vesicles: identity with Anchorin CII (Annexin V) and Annexin II," *Journal of Bone and mineral Research*, 7:807–19, 1992.

Goding, "Use of Staphylococcal Protein A as an immunological reagent," *Journal of Inmunological Methods*, 20:241–53, 1978.

Gonzales and Sognnaes, "Electron microscopy of dental calculus," *Science*, 131:156–8, 1960.

Green, Fry, Blondin, "Phospholipids as the molecular instruments of ion and solute transport in biological membranes," *Proceedings of the National Academy of Sciences USA*, 77:257–61, 1980.

Gross, "The cyanogen bromide reaction," *Methods in Enzymology*, 11:238–55, 1967.

Harlow and Lane, *Antibodies. A Laboratory Manual*. Cold Spring Harbor: Cold Spring Harbor Laboratory, 1988.

Hemming, Adams-Pearson, Maurer, Muller, Goris, Merlevede, et al., "a- and b-Forms of the 65 kDa subunit of protein phosphatase 2A have a similar 39 amino acid repeating sequence," *Biochemistry*, 29:3166–73, 1990.

Iakovidis, Cohen, Swain, Clem, Ghidoni, Everett, et al., "Oral micro-organisms and calcific aortic stenosis," *Circulation*, 86: 1–849, 1992.

Kessler, Vaughn, Fanestil, "Phosphate-binding proteolipid from brush border," *Journal of Biological Chemistry*, 257:14311–7, 1982.

Kessler, Vaughn, Fanestil, "Binding of calcium to the proteolipid phosphorin," *mineral and Electrolyte Metabolism*, 14:135–41, 1988.

Kessler, "Rapid isolation of antigens from cells with a staphylococcal protein A-antibody adsorbent: Parameters of the interaction of antibody-antigen complexes with protein A," *Journal of Immunology*, 115:1617–24, 1975.

Laemmli, "Cleavage of structural proteins during assembly of the head of bacteriophage $T_4$," *Nature*, 227:680–5, 1970.

Lees, Macklin, Chao, "A study of elastase peptides from bovine white matter proteolipid," *Neurochemical Research*, 6:1091–104, 1981.

Lees and Paxman "Modification of the Lowry procedure for the analysis of proteolipid protein," *Analytical Biochemistry*, 47:184–92, 1972.

Lie and Selvig, "Calcification of oral bacteria: an ultrastructural study of two strains of *Bacterionema matruchotii*," *Scandinavian Journal of Dental Research*, 82:8–18, 1974.

Lindmark, Thoren-Tolling, Sjoquist, "Binding of immunoglobulins to Protein A and immunoglobulin levels in mammalian sera," *Journal of Immunological Methods*, 62:1–13, 1983.

Magee and Schlesinger, "Fatty acid acylation of eukaryotic cell membrane proteins," *Biochimica et Biophysica Acta*, 694:279–89, 1982.

Malumbres, Gill, Martin, "Codon preference in *Corynebacteria*, *Gene*, 134:15–24, 1993.

Matsudaira, "Sequence from picomole quantities of proteins electroblotted onto polyvinylidene difluoride membranes," *Journal of Biological Chemistry*, 262:10035–8, 1987.

Matsudaira, "Limited N-terminal sequence analysis," *Methods in Enzymology*, 182:602–13, 1990.

McIlhinney, "Labeling of cell proteins with radioactive fatty acids and methods for studying palmitoyl-acyl transferase," In: *Lipid Modification of Proteins*. Hooper N M and Turner A J, editors. Oxford: Oxford University Press, pp. 15–36, 1992.

Moore, "Preparation and analysis of DNA," In: *Short Protocols in Molecular Biology*. Ausubel F M, editor. New York: John Wiley and Sons, pp. 2.1–2.12, 1992.

Neuhoff, Arold, Taube, Ehrhardt, "Improved staining of proteins in polyacrylamide gels including isoelectric focusing with clear background at nanogram sensitivity using Coomassie Brilliant Blue G-250 and R-250," *Electrophoresis*, 9:255–62, 1988.

Palfree and Elliot, "An enzyme-linked immunosorbent assay (ELISA) for detergent solubilized Ia glycoproteins using nitrocellulose membrane discs," *Journal of Immunological Methods*, 52:395–408, 1982.

Raggio, Boyan, Boskey, "In vivo hydroxyapatite formation induced by lipids," *Journal of Bone and mineral Research*, 1:409–15, 1986.

Regan, P. T., Malagelada, Jr., DiMagno, E. P., Glanzman, S. L., "Comparative effects of antacids, cimetidine and enteric coating on the therapeutic response to oral enzymes in severe pancreatic insufficiency", *New England Journal of Medicine*, 297:854–8, 1977.

Rizzo, Martin, Scott, Mergenhagen, "Mineralization of bacteria," *Science*, 135:439–41, 1962.

Ross and Peters, "Double staining to increase the sensitivity of protein detection in polyacrylamide gels," *BioTechniques*, 9:532–3, 1990.

Rost and Sander, "Prediction of protein secondary structure at better that 70% accuracy," Journal of Molecular Biology, 232:584–99, 1993.

Sambrook, Fritsch, Maniatis, *Molecular Biology. A Laboratory Manual*. Cold Spring Harbor: Cold Spring Harbor Laboratory Press, 1989.

Schägger and Von Jagow, "Tricine-sodium dodecylsulfate-polyacrylamide gel electrophoresis for the separation of proteins in the range from 1 to 100 kDa," *Analytical Biochemistry*, 166:368–79, 1987.

Streckfuss, Smith, Brown, Campbell "Calcification of selected strains of *Streptococcus mutans* and *Streptococcus sanguis*," *Journal of Bacteriology*, 120:502–6, 1974.

Swain, Renthal, Boyan, "Resolution of ion translocating proteolipid subclasses active in bacterial calcification," *Journal of Dental Research*, 68:1094–7, 1989.

Swain and Boyan, "Ion-translocating properties of calcifiable proteolipids," *Journal of Dental Research*, 67:526–30, 1988.

Swain and Boyan, "Ion-transport properties of membrane proteins associated with microbial calcification," In: *Recent Advances in the Study of Dental Calculus*. Ten Cate J M, editor. Oxford, UK: IRL Press, pp. 37–44, 1989.

Turner, "The diversity of lipid modifications of proteins," In: *Lipid Modifications of Proteins*. Hooper N M and Turner A J, editors. Oxford: Oxford University Press, pp. 1–13, 1992.

Vogel, Boyan-Salyers, Campbell, "Protein-phospholipid interactions in biological calcification," *Metabolic Bone Disease and Related Research*, 1:149–53, 1978.

Vogel and Boyan-Salyers, "Acidic lipids associated with the local mechanism of calcification," *Clinical Orthopaedics and Related Research* 118:230–41, 1976.

Vogel and Smith, "Calcification of membranes isolated from *Bacterionema matruchotii*," *Journal of Dental Research*, 55:1080–3, 1976.

Wasserman, Mandel, Levy, "In vitro calcification of dental calculus," *Journal of Periodontology*, 29:144–7, 1958.

Wu, Yoshimori, Genge, Sauer, Kirsch, Ishikawa, et al., "Characterization of the nucleational core complex responsible for the mineral induction by growth plate cartilage matrix vesicles,". *Journal of Biological Chemistry*, 268:25084–94, 1993.

Yuen, Hunkapiller, Wilson, Yuan, "Applications of tandem microbore liquid chromatography and sodium dodecyl sulfate-polyacrylamide gel electrophoresis/electroblotting in microsequence analysis," *Analytical Biochemistry*, 168:5–15, 1988.

Zander, Hazen, Scott, "Mineralization of dental calculus," *Proceedings of the Society for Experimental Biology and Medicine*, 103:257–60, 1960.

What is claimed is:

1. An isolated polynucleotide segment comprising a nucleic acid sequence that encodes a polypeptide comprising the amino acid sequence of SEQ ID NO:1.

2. The polynucleotide of claim 1, comprising the nucleic acid sequence of SEQ ID NO:3.

3. An isolated polynucleotide segment comprising a nucleic acid sequence that encodes a polypeptide comprising the amino acid sequence of SEQ ID NO:8.

4. The polynucleotide of claim 3, comprising the nucleic acid sequence of SEQ ID NO:6.

5. An isolated polynucleotide segment comprising a nucleic acid sequence of at least 20 contiguous nucleotides of SEQ ID NO:3.

6. The isolated polynucleotide of claim 5 comprising a nucleic acid sequence of at least 30 contiguous nucleotides of SEQ ID NO:3.

7. The isolated polynucleotide of claim 6, comprising a nucleic acid sequence at least 40 contiguous nucleotides of SEQ ID NO:3.

8. The isolated polynucleotide of claim 7, comprising a nucleic acid sequence at least 50 contiguous nucleotides of SEQ ID NO:3.

9. The isolated polynucleotide of claim 8, comprising a nucleic acid sequence at least 100 contiguous nucleotides of SEQ ID NO:3.

10. The isolated polynucleotide of claim 9, comprising the nucleic acid sequence of SEQ ID NO:3.

11. An isolated polynucleotide segment comprising the full complement of SEQ ID NO:3.

12. The polynucleotide of claim 1 or 3, wherein said polynucleotide comprises DNA.

13. The polynucleotide of claim 1 or 3, wherein said polynucleotide comprises RNA.

14. A vector comprising an isolated nucleic acid sequence that encodes a polypeptide comprising the amino acid sequence of SEQ ID NO:1 or SEQ ID NO:8.

15. The vector of claim 14, comprising the nucleic acid sequence of SEQ ID NO:3 or SEQ ID NO:6.

16. An isolated host cell comprising the polynucleotide of claim 1 or 3 or the vector of claim 14.

17. An isolated oligonucleotide having the sequence of SEQ ID NO:9, SEQ ID NO:10, SEQ ID NO:11 or SEQ ID NO:12.

* * * * *

UNITED STATES PATENT AND TRADEMARK OFFICE
CERTIFICATE OF CORRECTION

PATENT NO. : 5,989,907
DATED : November 23, 1999
INVENTOR(S) : Boyan et al.

It is certified that error appears in the above-identified patent and that said Letters Patent is hereby corrected as shown below:

<u>Title page,</u>
Item [60], Related U.S. Application Data, delete "Jan. 11" and insert -- Jan. 10 -- therefor.

Signed and Sealed this

Twelfth Day of November, 2002

*Attest:*

*Attesting Officer*

JAMES E. ROGAN
*Director of the United States Patent and Trademark Office*